United States Patent [19]

Römer et al.

[11] Patent Number: 4,505,837
[45] Date of Patent: Mar. 19, 1985

[54] LIQUID CRYSTALLINE PHENYLCYCLOHEXENE DERIVATIVES

[75] Inventors: Michael Römer, Rodgau; Ludwig Pohl, Darmstadt; Rudolf Eidenschink, Dieburg, all of Fed. Rep. of Germany

[73] Assignee: Merck Patent Gesellschaft mit beschränkter Haftung, Darmstadt, Fed. Rep. of Germany

[21] Appl. No.: 478,424

[22] Filed: Mar. 24, 1983

Related U.S. Application Data

[63] Continuation of Ser. No. 236,351, Feb. 20, 1981, abandoned.

[30] Foreign Application Priority Data

Feb. 22, 1980 [DE] Fed. Rep. of Germany ....... 3006666

[51] Int. Cl.³ .............. G09K 3/34; G02F 1/13; C07C 13/28; C07C 21/24; C07C 25/13; C07C 43/21; C07C 69/03; C07C 121/75
[52] U.S. Cl. ................... 252/299.6; 252/299.5; 252/299.63; 252/299.64; 252/299.66; 252/299.67; 350/350 R; 350/350 S; 428/1; 260/463; 260/465 D; 570/129; 585/23; 568/642; 568/631; 560/138; 560/102
[58] Field of Search .......... 350/350 R, 350 S; 252/299.5, 299.6, 299.66, 299.63, 299.67, 299.64; 428/1

[56] References Cited

U.S. PATENT DOCUMENTS

| | | | |
|---|---|---|---|
| 3,767,289 | 10/1973 | Aviram et al. | 252/299.6 |
| 4,130,502 | 12/1978 | Eidenschink et al. | 252/299.63 |
| 4,137,192 | 1/1979 | Matsufuji | 252/299.66 |
| 4,154,697 | 5/1979 | Eidenschink et al. | 252/299.63 |
| 4,207,252 | 6/1980 | Sato et al. | 252/299.6 |
| 4,211,666 | 7/1980 | Inukai et al. | 252/299.66 |
| 4,222,887 | 9/1980 | Matsufuji | 252/299.63 |
| 4,227,778 | 10/1980 | Raynes | 252/299.65 |
| 4,229,315 | 10/1980 | Krause et al. | 252/299.63 |
| 4,302,352 | 11/1981 | Eidenschink et al. | 252/299.63 |
| 4,330,426 | 5/1982 | Eidenschink et al. | 252/299.63 |
| 4,331,552 | 5/1982 | Eidenschink et al. | 252/299.5 |
| 4,405,488 | 9/1983 | Sugimori et al. | 252/299.63 |
| 4,422,951 | 12/1983 | Sugimori et al. | 252/299.63 |

FOREIGN PATENT DOCUMENTS

| | | | |
|---|---|---|---|
| 56-68636 | 6/1981 | Japan | 252/299.5 |
| 56-150030 | 11/1981 | Japan | 252/299.5 |
| 57-4927 | 1/1982 | Japan | 252/299.6 |
| 57-11935 | 1/1982 | Japan | 252/299.6 |
| 57-40429 | 3/1982 | Japan | 252/299.66 |
| 57-165326 | 10/1982 | Japan | 252/299.63 |
| 2078727 | 1/1982 | United Kingdom | 252/299.6 |

Primary Examiner—Teddy S. Gron
Attorney, Agent, or Firm—Millen & White

[57] ABSTRACT

A phenylcyclohexene of the formula

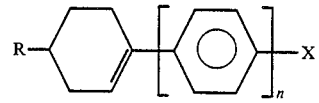

wherein n is 1 or 2, X is —H, —R, —OR, —OCOR, —OCOOR, —CF₃ or —F, and when n is 1, X can also be

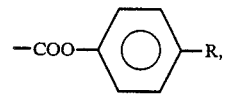

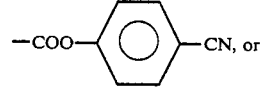

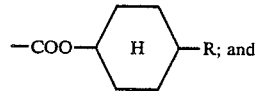

R is alkyl of 1-8 C atoms and when two R groups are present they can be the same or different, has valuable liquid crystalline properties.

16 Claims, No Drawings

LIQUID CRYSTALLINE PHENYLCYCLOHEXENE DERIVATIVES

This is a continuation of application Ser. No. 236,351 filed Feb. 20, 1981, now abandoned.

BACKGROUND OF THE INVENTION

The properties of nematic or nematic-cholesteric liquid crystalline materials are increasingly utilized for electro-optical display elements wherein significant changes are effected in the optical properties of such materials, such as light absorption, light scattering, birefringence, reflectance or color, under the influence of electric fields. The functioning of display elements of this type is based, for example, on the phenomena of dynamic scattering, the deformation of aligned phases (DAP effect), the Schadt-Helfrich effect in the twisted cell or the cholesteric-nematic phase transition.

For the technical application of these effects in electronic components, liquid crystalline dielectrics are required which must fulfill a large number of requirements. Chemical resistance to moisture, air and physical influences, such as heat, and electric fields is of particular importance. Industrially usable liquid crystalline dielectrics are also required to have a liquid crystalline mesophase in the temperature range from at least $+10°$ C. to $+50°$ C., preferably from $0°$ to $60°$ C., and the lowest possible viscosity at room temperature, which preferably should not exceed $70 \times 10^{-3}$ Pa.s. Finally, they must not have any characteristic absorption in the visible spectrum, i.e., they must be colorless.

A number of liquid crystalline compounds has already been disclosed. These fulfill the stability demands made for dielectrics intended for electronic components, and are also colorless. They include, in particular, the p,p'-disubstituted phenyl benzoates described in German Offenlegungsschrift No. 2,139,628 and the p,p'-disubstituted phenylcyclohexane derivatives described in German Offenlegungsschrift No. 2,636,684. In the two classes of compounds mentioned, and also in other known series of compounds having a liquid crystalline mesophase, there are no individual compounds which form a liquid crystalline nematic mesophase in the required temperature range from $10°$ C. to $60°$ C. Therefore, as a rule, mixtures of two or more compounds are prepared in order to obtain substances which can be used as liquid crystalline dielectrics.

For this purpose, a compound having a low melting point and clear point is usually mixed with another compound having a markedly higher melting point and clear point. This normally gives a mixture, the melting point of which is below that of the lower-melting component, while the clear point is between the clear points of the components. It is, however, not easy to prepare optimum dielectrics in this way, since the components having the high melting points and clear points frequently also impart a high viscosity to the mixtures. As a result, the switching times of the electro-optical display elements produced with these mixtures are undesirably extended.

Among the known base material for liquid crystalline dielectrics, the mentioned p,p'-disubstituted phenylcyclohexanes are distinguished by a particularly low viscosity. As is known, the cyclohexane ring in compounds of this type can be present either in the cis-configuration or in the trans-configuration; however, liquid crystalline properties have only been found for the compounds having the trans-configuration. In the conventional syntheses of liquid-crystalline compounds having this structure, an isomerization reaction and/or an isomer separation, which is sometimes associated with considerable loss of substances, is therefore generally necessary. As a result, the manufacture of the phenylcyclohexanes becomes expensive.

SUMMARY OF THE INVENTION

Accordingly, it is an object of this invention to provide liquid crystalline dielectrics which, to the greatest possible extent, have properties at least as good as those of the known liquid crystalline dielectrics based on phenylcyclohexanes, and at the same time can be produced at low cost and hence more economically.

Upon further study of the specification and appended claims, further objects and advantages of this invention will become apparent to those skilled in the art.

These objects have been attained by providing phenylcyclohexene derivatives of formula (I)

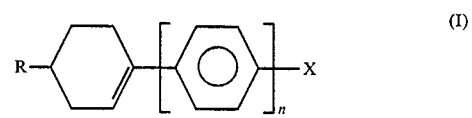

wherein n is 1 or 2, X denotes —H, —R, —OR, —OCOR, —OCOOR, —CF$_3$ or —F or, if n is 1, also denotes

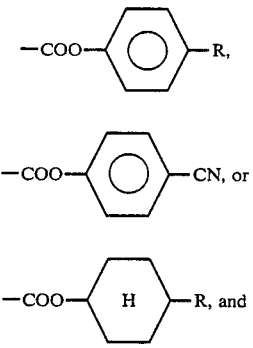

R denotes alkyl having 1–8 C atoms.

These compounds are virtually equivalent to the phenylcyclohexanes of German Offenlegungsschrift No. 2,636,684 (U.S. Pat. No. 4,130,502) or the cyclohexane derivatives of German Offenlegungsschrift No. 2,800,553 (U.S. Pat. No. 4,229,315) in all of the properties essential for use as components of liquid crystalline dielectrics. However, at the same time, they can be manufactured at markedly lower cost and hence more economically. In particular, due to the double bond in the cyclohexene ring, cis-trans isomerism is no longer possible, whereby the need for an isomerization reaction and/or isomer separation during the synthesis can be obviated.

The invention, thus, relates to the phenyl-cyclohexene derivatives of formula (I), to their manufacture and to their use as components of liquid-crystalline dielectrics. Furthermore, the invention relates to liquid crystalline dielectrics containing at least one phenylcyclohexene derivative of formula (I) and to electrooptical display elements which are based on liquid crystal cells and which contain liquid-crystalline dielectrics of this type.

DETAILED DISCUSSION

In the compounds of this invention, the radical R, as the wing group per se or as part of wing groups, denotes straight-chain or branched alkyl groups of 1 to 8 C atoms. If a compound of this invention contains two radicals R, they may be the same or different; however, at most one of these should be a branched alkyl group. Those compounds of the formula (I) in which both wing groups are straight-chain alkyl groups or contain straight-chain alkyl groups, are preferred, since these compounds as a rule have markedly higher clear points.

Compounds of this invention of formula (I) having a branched wing group are occasionally important because of a higher solubility in the conventional liquid crystalline base materials, and particularly as chiral doping substances if they possess optical activity due to the chain branching. Such branched substituents should not contain more than one chain branching.

Preferred branched radicals are those in which a methyl or ethyl group is located in the 1-, 2- or 3-position on a relatively long carbon chain, for example, 2-methylpropyl, 2-methylbutyl, 1-methylbutyl, 2-methylpentyl, 3-methylpentyl, 2-ethylhexyl, 2-methylhexyl or 1-methylheptyl. According to the definition of formula (I), the wing groups of the compounds of this invention together can contain up to 16 carbon atoms. Among these, those compounds are preferred in which the wing groups together contain 2 to 14, in particular, 4 to 12 carbon atoms.

When the wing group X denotes F or $CF_3$, the resultant compounds of this invention have a markedly positive dielectric anisotropy (DCA). Compounds from this group are preferably used in dielectrics for the twisted nematic cell or for display elements based on the cholesteric-nematic phase transition.

Preferred compounds of this invention are those of formula (Ia)

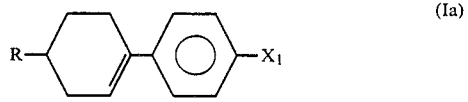

wherein $X_1$ is —R, —OR or —OCOR and R is alkyl of 1–8 C atoms.

These compounds have DCA values of around zero and are therefore suitable as base substances of dielectrics for display elements based on dynamic scattering and the DAP effect.

Further preferred compounds of this invention are the cyclohexenylbiphenyls of formula (Ib)

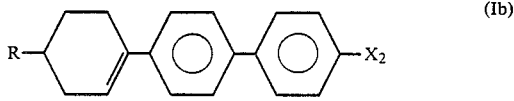

wherein $X_2$ is —H, —R, —OR, —OCOR, —F or —$CF_3$ and R is alkyl of 1–8 C atoms.

These substances have high clear points which usually are markedly above those of the analogous cyclohexyl derivatives; for this reason, they are especially useful as additives for dielectrics based on cyclohexenylbenzene derivatives of formula (I) in order to increase the clear points. The cyclohexenylbenzoic acid esters of formula (Ic)

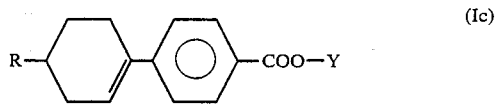

wherein Y is 4-cyanophenyl, 4-(R)-phenyl or trans-4-(R)-cyclohexyl and R is alkyl of 1–8 C atoms, are likewise preferred within the scope of the present inventions, and are also useful for this purpose. The trans-conformation of the cyclohexane ring occuring as Y group is shown in the formula by a black dot at the right side of the cyclohexane ring.

With respect to their use as components of liquid crystalline dielectrics, the compounds of this invention of formula (I), very largely have the same advantageous properties as the analogous cyclohexane derivatives.

A clear advantage of the phenylcyclohexene derivatives of this invention, compared with the saturated analog, is their higher optical anisotropy. In liquid crystalline dielectrics having a higher optical anisotropy, the risk of troublesome interference phenomena occurring in the thin liquid crystal layers customary in display elements is markedly reduced.

According to this invention, the compounds of formula (I) can be prepared by reacting a Grignard compound of formula (II)

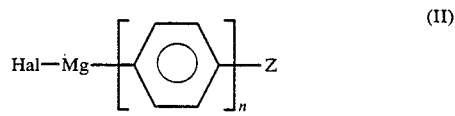

wherein n is 1 or 2, Hal is —Cl or —Br and Z is —H, —R, —OR, —F or a group which is resistant to Grignard reagents and can readily be converted to a hydroxyl or carboxyl group, with a cyclohexanone of formula (III)

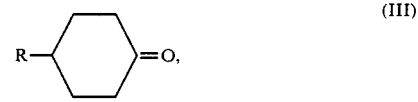

treating the alcohol obtained by hydrolysis from the resulting reaction mixture with a dehydrating agent and, if appropriate, subsequently converting an undesired group Z to a desired group X in a manner known per se.

In this process, the Grignard compounds of formula (II) can be prepared in a manner known per se from the corresponding halogenobenzenes, in particular chlorobenzene derivatives and preferably bromobenzene derivatives or halogenobiphenyl derivatives by reaction with magnesium in an ether, preferably diethyl ether, tetrahydrofuran or anisole. Suitable groups Z which are resistant to Grignard reagents especially include the benzyloxy group for the conversion to the hydroxyl group and the 4,4-dimethyl- or 4,4,5,5-tetramethyl-oxazolin-2-yl group for the conversion to the carboxyl group.

The reaction of the Grignard compounds of formula (II) with the cyclohexanones of formula (III), as well as the subsequent hydrolysis, are carried out in the manner conventional for reactions of this type. The alcohols of formula (IV)

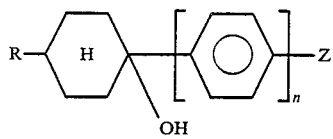

are isolated from the hydrolyzed reaction mixture in the conventional manner, e.g., by extraction with a water-immiscible solvent suitable for this purpose, for example, diethyl ether, toluene or chloroform. They are then converted by treatment with a strong acid, for example, sulfuric acid, phosphoric acid or p-toluenesulfonic acid, if necessary with heating, to the phenylcyclohexene derivatives of formula (V)

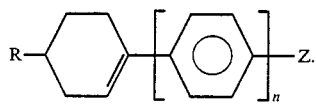

In the formulae (IV) and (V), the symbols R, n and Z are as defined for formula (II). When Z is —H, —R, —OR or —F, these compounds already are the end products of formula (I).

To prepare the compounds of formula (I), in which X is an alkanoyloxy group —OCOR or an alkoxycarbonyloxy group —OCOOR, the starting materials are preferably the compounds of formula (V) in which Z is benzyloxy. This benzyloxy group is hydrolytically or hydrogenolytically eliminated in a manner known per se, and the cyclohexen-1-yl-phenol or -biphenylol, thus obtained, is esterified by standard methods with, for example, an alkanoyl chloride or chloroformate respectively.

The synthesis of the compounds of formula (I) in which X is trifluoromethyl ($CF_3$), preferably starts from the compounds of formula (V), wherein Z is 4,4-dimethyl- or 4,4,5,5-tetramethyl-oxazolin-2-yl. By treatment with an acid, this compound is converted to the corresponding carboxylic acid (VI)

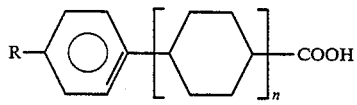

wherein R and n are as defined above. This carboxylic acid is then converted to the trifluoromethyl compound in a manner known per se, for example, by successive reactions with phosphorus pentachloride and antimony trifluoride.

The compounds of formula (Ic) can be obtained from the carboxylic acids of formula (VI) in which n is 1, by esterification with a trans-cyclohexanol derivative or phenol derivative H-O-Y. In these esterification reactions, the process conditions known per se are applied, such as are described, for example, in German Offenlegungsschrift No. 2,800,553.

A large percentage of the starting materials for the above-described syntheses of the compounds of this invention is described in the literature; if they are not explicitly mentioned in the literature, for example, higher homologs of the Grignard compounds (II) (n=2, Z=heptyl, octyl, fluorine or the like), they can be prepared without difficulty by the processes indicated in the literature for the preparation of the base compounds.

The liquid crystalline dielectrics of this invention comprise two or more components, including at least one of formula (I). Dielectrics of this invention can, however, also consist exclusively of compounds of formula (I)—apart from doping substances or additives which may optionally also be present and which do not themselves have to be liquid crystalline. Other optional components are preferably nematic or nematogenic substances from the classes of azobenzenes, azoxybenzenes, biphenyls, Schiff bases, in particular benzylidene derivatives, phenyl benzoates, phenylpyrimidines, phenylcyclohexanes, optionally halogenated stilbenes, diphenylacetylene derivatives, diphenylnitrones, phenyl- or cyclohexyl-naphthalenes which can also be partially hydrogenated in the naphthalene portion and can contain nitrogen atoms, as well as substituted cinnamic acids. The most important compounds, which can be used as such other components, can be characterized by formula (VII):

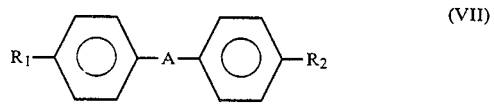

wherein A is

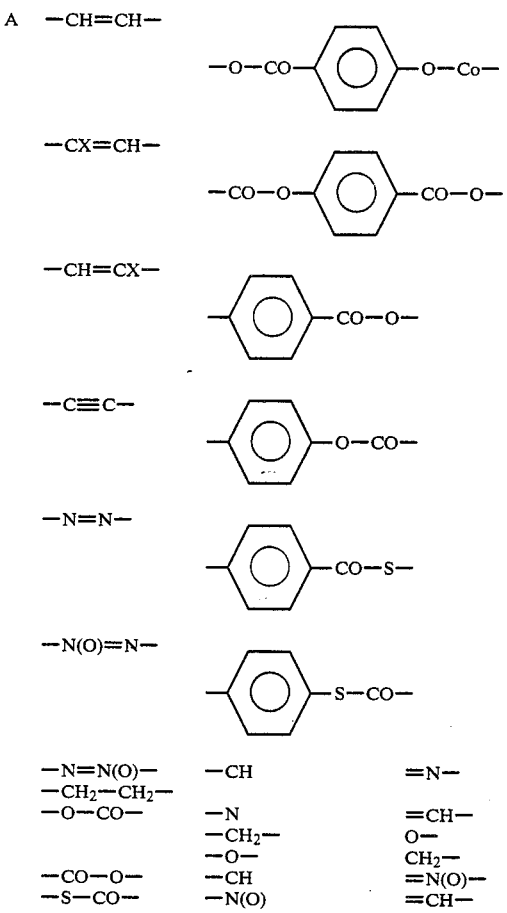

—CO—S— or a 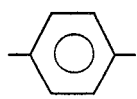

C—C single bond.

Other possible components of the dielectrics of this invention are those compounds of formula (VII) in which one or more phenyl rings are replaced by a corresponding number of trans-cyclohexyl rings; one of these rings can also be a 2,5-disubstituted pyrimidine ring or an optionally partially hydrogenated 2,6-disubstituted naphthalene or quinazoline system.

$X'$ is halogen, preferably Cl, or —CN. $R_1$ and $R_2$ are identical or different and can be alkyl, alkoxy, alkanoyl, alkanoyloxy or alkoxycarbonyl radicals of up to 18, preferably up to 8, C atoms; moreover, one of these radicals can also be —CN, —NC, $NO_2$, $CF_3$ or halogen.

In most of these compounds, $R_1$ and $R_2$ are preferably different, one of the radicals being an alkyl or alkoxy group in most cases. A large number of other variants of the envisaged substituents, however, are also common. Many such substances are commercially available.

The dielectrics of this invention contain as a rule at least 30, preferably 50-99, in particular 60-98, percent by weight of the compounds of formula (I) and, if appropriate, (VII). Of these, preferably at least 5 percent by weight, in most cases even 10 or more percent by weight, is constituted by one or more compounds of formula (I). The invention also comprises those liquid crystalline dielectrics to which only less than 5 percent by weight, for example 0.1 to 3 percent by weight, of one or more compounds of formula (I) have been added, for example, for doping purposes.

The preparation of the dielectrics of this invention is carried out in a manner conventional per se. As a rule, the desired quantity of the components used in a smaller quantity is dissolved in the component representing the main constituent, advantageously at elevated temperature. If a temperature above the clear point of the main constituent is chosen, the completeness of the solution process can be observed with particular ease.

It is also possible, however, to mix solutions of the components of formula (I) and, if appropriate, (VII), in a suitable organic solvent, for example, acetone, chloroform or methanol, and, after thorough mixing, to remove the solvent, for example, by distillation under reduced pressure. Of course, it is necessary in this procedure to take care that no impurities or undesired doping substances are introduced by the solvent.

The liquid crystalline dielectrics of this invention can be modified by suitable conventional additives in such a way that they can be used in all hitherto disclosed types of liquid crystal display elements. Additives of this type are known to those skilled in the art and are extensively described in the relevant literature. For example, substances can be added for varying the dielectric anisotropy, the viscosity, the conductivity and/or the orientation of the nematic phases. Substances of this type are described, for example, in German Offenlegungsschriften Nos. 2,209,127; 2,240,864; 2,321,632; 2,338,281; 2,535,046; 2,637,430 and 2,900,312.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth in degrees Celsius; unless otherwise indicated; all parts and percentages are by weight.

In the examples, m.p. denotes the melting point, and c.p. denotes the clear point, of a liquid crystalline substance in degrees centigrade; boiling points are marked b.p.

EXAMPLE 1

A solution of 15.7 g of bromobenzene in 20 ml of tetrahydrofuran is added dropwise with stirring over the course of 30 minutes to 2.4 g of magnesium turnings in 20 ml of tetrahydrofuran; the resulting Grignard solution is heated to the boil for a further 2 hours with stirring. Subsequently, a solution of 14 g of 4-n-propylcyclohexanone in 20 ml of tetrahydrofuran is added dropwise with stirring and the reaction mixture is then heated to the boil for a further 2 hours with stirring. 40 ml of 10% strength aqueous hydrochloric acid is then added over the course of 10 minutes with stirring and cooling, and the reaction mixture is extracted three times with 50 ml of diethyl ether. The combined extracts are dried over magnesium sulphate and evaporated. The residue is dissolved in 50 ml of acetone and the solution is heated to the boil with 1 g of p-toluenesulphonic acid for 2 hours. Subsequently, 250-ml of water is added and the reaction mixture is extracted three times with 50 ml of diethyl ether. The combined extracts are washed with 5% strength aqueous sodium bicarbonate solution and water, dried over magnesium sulphate and evaporated. The (4-n-propylcyclohexen-1-yl)-benzene which remains is distilled under reduced pressure; 11 g of a colorless oil of b.p. 180°–185°/13 mbar is obtained. The following are prepared analogously:

(4-methylcyclohexen-1-yl)-benzene,
(4-ethylcyclohexen-1-yl)-benzene,
(4-n-butylcyclohexen-1-yl)-benzene,
(4-n-pentylcyclohexen-1-yl)-benzene,
(4-n-hexylcyclohexen-1-yl)-benzene,
(4-n-heptylcyclohexen-1-yl)-benzene,
(4-n-octylcyclohexen-1-yl)-benzene,
[4-(1-methylhexyl)-cyclohexen-1-yl]-benzene,
[4-(2-methylbutyl)-cyclohexen-1-yl]-benzene,
[4-(3-ethylpentyl)-cyclohexen-1-yl]-benzene, 4-(4-methylcyclohexen-1-yl)-fluorobenzene,
4-(4-ethylcyclohexen-1-yl)-fluorobenzene,
4-(4-n-propylcyclohexen-1-yl)-fluorobenzene,
4-(4-n-butylcyclohexen-1-yl)-fluorobenzene,
4-(4-n-pentylcyclohexen-1-yl)-fluorobenzene,
4-(4-n-hexylcyclohexen-1-yl)-fluorobenzene,
4-(4-n-heptylcyclohexen-1-yl)-fluorobenzene,
4-(4-n-octylcyclohexen-1-yl)-fluorobenzene,
4-[4-(1-methylhexyl)-cyclohexen-1-yl]-fluorobenzene,
4-[4-(2-methylbutyl)-cyclohexen-1-yl]-fluorobenzene and
4-[4-(3-ethylpentyl)-cyclohexen-1-yl]-fluorobenzene.

EXAMPLE 2

A solution of 780 g of 4-ethoxybromobenzene in 1,900 ml of tetrahydrofuran is added dropwise to a well stirred suspension of 94.2 g of magnesium turnings in 364 ml of tetrahydrofuran at such a rate that the reaction mixture is constantly boiling gently. The Grignard solution obtained is stirred for an additional 2 hours at 60°; subsequently, a solution of 652 g of 4-n-pentylcyclohexanone in 728 ml of tetrahydrofuran is added dropwise and the reaction mixture is heated to the boil for an additional 2 hours with stirring. After cooling, it is poured into a mixture of 442 ml of 36% strength aqueous hydrochloric acid and 1,500 ml of water, and the resulting mixture is vigorously stirred for 15 minutes and allowed to settle. The organic phase is separated off, and the aqueous phase is extracted twice with 400 ml of toluene. The combined organic phases are washed twice with 1,500 ml of water, filtered and concentrated under reduced pressure, until a viscous oil remains. This residue is dissolved in 1,500 g of acetone and the solution is heated to the boil with 63 g of p-toluenesulphonic acid for 3 hours. After cooling, the 4-(4-n-pentylcyclohexen-1-yl)-phenetole which has crystallized out is filtered off and recrystallized from ethanol; yield 212 g. m.p. 70.1°, c.p. 70.0°.

The following are prepared analogously:
4-(4-methylcyclohexen-1-yl)-anisole,
4-(4p-ethylcyclohexen-1-yl)-anisole,
4-(4-n-propylcyclohexen-1-yl)-anisole,
4-(4-n-butylcyclohexen-1-yl)-anisole,
4-(4-n-pentylcyclohexen-1-yl)-anisole,
4-(4-n-hexylcyclohexen-1-yl)-anisole,
4-(4-n-heptylcyclohexen-1-yl)-anisole,
4-(4-n-octylcyclohexen-1-yl)-anisole,
4-[4-(1-methylhexyl)-cyclohexen-1-yl]-anisole,
4-[4-(2-methylbutyl)-cyclohexen-1-yl]-anisole,
4-[4-(3-ethylpentyl)-cyclohexen-1-yl]-anisole,
4-(4-methylcyclohexen-1-yl)-phenetole,
4-(4-ethylcyclohexen-1-yl)-phenetole,
4-(4-n-propylcyclohexen-1-yl)-phenetole,
4-(4-n-butylcyclohexen-1-yl)-phenetole,
4-(4-n-hexylcyclohexen-1-yl)-phenetole,
4-(4-n-heptylcyclohexen-1-yl)-phenetole,
4-(4-n-octylcyclohexen-1-yl)-phenetole,
4-[4-(1-methylhexyl)-cyclohexen-1-yl]-phenetole,
4-[4-(2-methylbutyl)-cyclohexen-1-yl]-phenetole,
4-[4-(3-ethylpentyl)-cyclohexen-1-yl]-phenetole, 4-(4-methylcyclohexen-1-yl)-n-propoxybenzene,
4-(4-ethylcyclohexen-1-yl)-n-propoxybenzene,
4-(4-n-propylcyclohexen-1-yl)-n-propoxybenzene,
4-(4-n-butylcyclohexen-1-yl)-n-propoxybenzene,
4-(4-n-pentylcyclohexen-1-yl)-n-propoxybenzene,
4-(4-n-hexylcyclohexen-1-yl)-n-propoxybenzene,
4-(4-n-heptylcyclohexen-1-yl)-n-propoxybenzene,
4-(4-n-octylcyclohexen-1-yl)-n-propoxybenzene,
4-[4-(1-methylhexyl)-cyclohexen-1-yl]-n-propoxybenzene,
4-[4-(2-methylbutyl)-cyclohexen-1-yl]-n-propoxybenzene,
4-[4-(3-ethylpentyl)-cyclohexen-1-yl]-n-propoxybenzene,
4-(4-methylcyclohexen-1-yl)-n-butoxybenzene,
4-(4-ethylcyclohexen-1-yl)-n-butoxybenzene,
4-(4-n-propylcyclohexen-1-yl)-n-butoxybenzene, m.p. 47.7°, c.p. 64.0°;
4-(4-n-butylcyclohexen-1-yl)-n-butoxybenzene,
4-(4-n-pentylcyclohexen-1-yl)-n-butoxybenzene, m.p. 36.4°, c.p. 76.4°;
4-(4-n-hexylcyclohexen-1-yl)-n-butoxybenzene,
4-(4-n-heptylcyclohexen-1-yl)-n-butoxybenzene,
4-(4-n-octylcyclohexen-1-yl)-n-butoxybenzene,
4-[4-(1-methylhexyl)-cyclohexen-1-yl]-n-butoxybenzene,
4-[4-(2-methylbutyl)-cyclohexen-1-yl]-n-butoxybenzene,
4-[4-(3-ethylpentyl)-cyclohexen-1-yl]-n-butoxybenzene,
4-(4-methylcyclohexen-1-yl)-n-pentyloxybenzene,
4-(4-ethylcyclohexen-1-yl)-n-pentyloxybenzene,
4-(4-n-propylcyclohexen-1-yl)-n-pentyloxybenzene,
4-(4-n-butylcyclohexen-1-yl)-n-pentyloxybenzene,
4-(4-n-pentylcyclohexen-1-yl)-n-pentyloxybenzene,
4-(4-n-hexylcyclohexen-1-yl)-n-pentyloxybenzene,
4-(4-n-heptylcyclohexen-1-yl)-n-pentyloxybenzene,
4-(4-n-octylcyclohexen-1-yl)-n-pentyloxybenzene,
4-[4-(1-methylhexyl)-cyclohexen-1-yl]-n-pentyloxybenzene,
4-[4-(2-methylbutyl)-cyclohexen-1-yl]-n-pentyloxybenzene,
4-[4-(3-ethylpentyl)-cyclohexen-1-yl]-n-pentyloxybenzene, 4-(4-methylcyclohexen-1-yl)-n-hexyloxybenzene,
4-(4-ethylcyclohexen-1-yl)-n-hexyloxybenzene,
4-(4-n-propylcyclohexen-1-yl)-n-hexyloxybenzene,
4-(4-n-butylcyclohexen-1-yl)-n-hexyloxybenzene,
4-(4-n-pentylcyclohexen-1-yl)-n-hexyloxybenzene,
4-(4-n-hexylcyclohexen-1-yl)-n-hexyloxybenzene,
4-(4-n-heptylcyclohexen-1-yl)-n-hexyloxybenzene,
4-(4-n-octylcyclohexen-1-yl)-n-hexyloxybenzene,
4-[4-(1-methylhexyl)-cyclohexen-1-yl]-n-hexyloxybenzene,
4-[4-(2-methylbutyl)-cyclohexen-1-yl]-n-hexyloxybenzene,
4-[4-(3-ethylpentyl)-cyclohexen-1-yl]-n-hexyloxybenzene, 4-(4-methylcyclohexen-1-yl)-n-heptyloxybenzene,
4-(4-ethylcyclohexen-1-yl)-n-heptyloxybenzene,
4-(4-n-propylcyclohexen-1-yl)-n-heptyloxybenzene,
4-(4-n-butylcyclohexen-1-yl)-n-heptyloxybenzene,
4-(4-n-pentylcyclohexen-1-yl)-n-heptyloxybenzene,
4-(4-n-hexylcyclohexen-1-yl)-n-heptyloxybenzene,
4-(4-n-heptylcyclohexen-1-yl)-n-heptyloxybenzene,
4-(4-n-octylcyclohexen-1-yl)-n-heptyloxybenzene,
4-[4-(1-methylhexyl)-cyclohexen-1-yl]-n-heptyloxybenzene,
4-[4-(2-methylbutyl)-cyclohexen-1-yl]-n-heptyloxybenzene,
4-[4-(3-ethylpentyl)-cyclohexen-1-yl]-n-heptyloxybenzene, 4-(4-methylcyclohexen-1-yl)-n-octyloxybenzene,
4-(4-ethylcyclohexen-1-yl)-n-octyloxybenzene,
4-(4-n-propylcyclohexen-1-yl)-n-octyloxybenzene,
4-(4-n-butylcyclohexen-1-yl)-n-octyloxybenzene,
4-(4-n-pentylcyclohexen-1-yl)-n-octyloxybenzene,
4-(4-n-hexylcyclohexen-1-yl)-n-octyloxybenzene,
4-(4-n-heptylcyclohexen-1-yl)-n-octyloxybenzene,
4-(4-n-octylcyclohexen-1-yl)-n-octyloxybenzene,
4-[4-(1-methylhexyl)-cyclohexen-1-yl]-n-octyloxybenzene,
4-[4-(2-methylbutyl)-cyclohexen-1-yl]-n-octyloxybenzene,
4-[4-(3-ethylpentyl)-cyclohexen-1-yl]-n-octyloxybenzene, 4-(4-methylcyclohexen-1-yl)-1-(2-ethylhexyloxy)-benzene,
4-(4-ethylcyclohexen-1-yl)-1-(2-ethylhexyloxy)-benzene, 4-(4-n-propylcyclohexen-1-yl)-1-(2-ethylhexyloxy)-benzene,
4-(4-n-butylcyclohexen-1-yl)-1-(2-ethylhexyloxy)-benzene,
4-(4-n-pentylcyclohexen-1-yl)-1-(2-ethylhexyloxy)-benzene,
4-(4-n-hexylcyclohexen-1-yl)-1-(2-ethylhexyloxy)-benzene,
4-(4-n-heptylcyclohexen-1-yl)-1-(2-ethylhexyloxy)-benzene,
4-(4-n-octylcyclohexen-1-yl)-1-(2-ethylhexyloxy)-benzene, 4-(4-methylcyclohexen-1-yl)-1-(1-methylbutoxy)-benzene,
4-(4-ethylcyclohexen-1-yl)-1-(1-methylbutoxy)-benzene,
4-(4-n-propylcyclohexen-1-yl)-1-(1-methylbutoxy)-benzene,
4-(4-n-butylcyclohexen-1-yl)-1-(1-methylbutoxy)-benzene,
4-(4-n-pentylcyclohexen-1-yl)-1-(1-methylbutoxy)-benzene,
4-(4-n-hexylcyclohexen-1-yl)-1-(1-methylbutoxy)-benzene,
4-(4-n-heptylcyclohexen-1-yl)-1-(1-methylbutoxy)-benzene,
4-(4-n-octylcyclohexen-1-yl)-1-(1-methylbutoxy)-benzene, 4-(4-methylcyclohexen-1-yl)-benzyloxybenzene,
4-(4-ethylcyclohexen-1-yl)-benzyloxybenzene,
4-(4-n-propylcyclohexen-1-yl)-benzyloxybenzene,
4-(4-n-butylcyclohexen-1-yl)-benzyloxybenzene,
4-(4-n-pentylcyclohexen-1-yl)-benzyloxybenzene, m.p. 79°, c.p. 104°,
4-(4-n-hexylcyclohexen-1-yl)-benzyloxybenzene,
4-(4-n-heptylcyclohexen-1-yl)-benzyloxybenzene,
4-(4-n-octylcyclohexen-1-yl)-benzyloxybenzene,
4-[4-(1-methylhexyl)-cyclohexen-1-yl]-benzyloxybenzene,
4-[4-(2-methylbutyl)-cyclohexen-1-yl]-benzyloxybenzene,
4-[4-(3-ethylpentyl)-cyclohexen-1-yl]-benzyloxybenzene, 4-(4-methylcyclohexen-1-yl)-toluene,
4-(4-ethylcyclohexen-1-yl)-toluene,
4-(4-n-propylcyclohexen-1-yl)-toluene,
4-(4-n-butylcyclohexen-1-yl)-toluene,
4-(4-n-pentylcyclohexen-1-yl)-toluene,
4-(4-n-hexylcyclohexen-1-yl)-toluene,
4-(4-n-heptylcyclohexen-1-yl)-toluene,
4-(4-n-octylcyclohexen-1-yl)-toluene,
4-[4-(1-methylhexyl)-cyclohexen-1-yl]-toluene,
4-[4-(2-methylbutyl)-cyclohexen-1-yl]-toluene,
4-[4-(3-ethylpentyl)-cyclohexen-1-yl]-toluene, 4-(4-methylcyclohexen-1-yl)-ethylbenzene,
4-(4-ethylcyclohexen-1-yl)-ethylbenzene,
4-(4-n-propylcyclohexen-1-yl)-ethylbenzene,
4-(4-n-butylcyclohexen-1-yl)-ethylbenzene,
4-(4-n-pentylcyclohexen-1-yl)-ethylbenzene,
4-(4-n-hexylcyclohexen-1-yl)-ethylbenzene,
4-(4-n-heptylcyclohexen-1-yl)-ethylbenzene,
4-(4-n-octylcyclohexen-1-yl)-ethylbenzene,
4-[4-(1-methylhexyl)-cyclohexen-1-yl]-ethylbenzene,
4-[4-(2-methylbutyl)-cyclohexen-1-yl]-ethylbenzene,
4-[4-(3-ethylpentyl)-cyclohexen-1-yl]-ethylbenzene, 4-(4-methylcyclohexen-1-yl)-n-propylbenzene,
4-(4-ethylcyclohexen-1-yl)-n-propylbenzene,
4-(4-n-propylcyclohexen-1-yl)-n-propylbenzene,
4-(4-n-butylcyclohexen-1-yl)-n-propylbenzene,
4-(4-n-pentylcyclohexen-1-yl)-n-propylbenzene,
4-(4-n-hexylcyclohexen-1-yl)-n-propylbenzene,
4-(4-n-heptylcyclohexen-1-yl)-n-propylbenzene,
4-(4-n-octylcyclohexen-1-yl)-n-propylbenzene,
4-[4-(1-methylhexyl)-cyclohexen-1-yl]-n-propylbenzene,
4-[4-(2-methylbutyl)-cyclohexen-1-yl]-n-propylbenzene,
4-[4-(3-ethylpentyl)-cyclohexen-1-yl]-n-propylbenzene, 4-(4-methylcyclohexen-1-yl)-n-butylbenzene,
4-(4-ethylcyclohexen-1-yl)-n-butylbenzene,
4-(4-n-propylcyclohexen-1-yl)-n-butylbenzene,
4-(4-n-butylcyclohexen-1-yl)-n-butylbenzene,
4-(4-n-pentylcyclohexen-1-yl)-n-butylbenzene,
4-(4-n-hexylcyclohexen-1-yl)-n-butylbenzene,
4-(4-n-heptylcyclohexen-1-yl)-n-butylbenzene,
4-(4-n-octylcyclohexen-1-yl)-n-butylbenzene,
4-[4-(1-methylhexyl)-cyclohexen-1-yl]-n-butylbenzene,
4-[4-(2-methylbutyl)-cyclohexen-1-yl]-n-butylbenzene,
4-[4-(3-ethylpentyl)-cyclohexen-1-yl]-n-butylbenzene, 4-(4-methylcyclohexen-1-yl)-n-pentylbenzene,
4-(4-ethylcyclohexen-1-yl)-n-pentylbenzene,
4-(4-n-propylcyclohexen-1-yl)-n-pentylbenzene,
4-(4-n-butylcyclohexen-1-yl)-n-pentylbenzene,
4-(4-n-pentylcyclohexen-1-yl)-n-pentylbenzene,
4-(4-n-hexylcyclohexen-1-yl)-n-pentylbenzene,
4-(4-n-heptylcyclohexen-1-yl)-n-pentylbenzene,
4-(4-n-octylcyclohexen-1-yl)-n-pentylbenzene,
4-[4-(1-methylhexyl)-cyclohexen-1-yl]-n-pentylbenzene,
4-[4-(2-methylbutyl)-cyclohexen-1-yl]-n-pentylbenzene,
4-[4-(3-ethylpentyl)-cyclohexen-1-yl]-n-pentylbenzene,
4-(4-methylcyclohexen-1-yl)-1-(2-methylbutyl)-benzene,
4-(4-ethylcyclohexen-1-yl)-1-(2-methylbutyl)-benzene,
4-(4-n-propylcyclohexen-1-yl)-1-(2-methylbutyl)-benzene,
4-(4-n-butylcyclohexen-1-yl)-1-(2-methylbutyl)-benzene,
4-(4-n-pentylcyclohexen-1-yl)-1-(2-methylbutyl)-benzene,
4-(4-n-hexylcyclohexen-1-yl)-1-(2-methylbutyl)-benzene,
4-(4-n-heptylcyclohexen-1-yl)-1-(2-methylbutyl)-benzene,
4-(4-n-octylcyclohexen-1-yl)-1-(2-methylbutyl)-benzene, 4-(4-methylcyclohexen-1-yl)-n-hexylbenzene,
4-(4-ethylcyclohexen-1-yl)-n-hexylbenzene,
4-(4-n-propylcyclohexen-1-yl)-n-hexylbenzene,
4-(4-n-butylcyclohexen-1-yl)-n-hexylbenzene,
4-(4-n-pentylcyclohexen-1-yl)-n-hexylbenzene,
4-(4-n-hexylcyclohexen-1-yl)-n-hexylbenzene,
4-(4-n-heptycyclohexen-1-yl)-n-hexylbenzene,
4-(4-n-octylcyclohexen-1-yl)-n-hexylbenzene,
4-[4-(1-methylhexyl)-cyclohexen-1-yl]-n-hexylbenzene,
4-[4-(2-methylbutyl)-cyclohexen-1-yl]-n-hexylbenzene,
4-[4-(3-ethylpentyl)-cyclohexen-1-yl]-n-hexylbenzene, 4-(4-methylcyclohexen-1-yl)-n-heptylbenzene,
4-(4-ethylcyclohexen-1-yl)-n-heptylbenzene,
4-(4-n-propylcyclohexen-1-yl)-n-heptylbenzene,
4-(4-n-butylcyclohexen-1-yl)-n-heptylbenzene,
4-(4-n-pentylcyclohexen-1-yl)-n-heptylbenzene,
4-(4-n-hexylcyclohexen-1-yl)-n-heptylbenzene,
4-(4-n-heptylcyclohexen-1-yl)-n-heptylbenzene,
4-(4-n-octylcyclohexen-1-yl)-n-heptylbenzene,
4-[4-(1-methylhexyl)-cyclohexen-1-yl]n-heptylbenzene,
4-[4-(2-methylbutyl)-cyclohexen-1-yl]-n-heptylbenzene,
4-[4-(3-ethylpentyl)-cyclohexen-1-yl]-n-heptylbenzene, 4-(4-methylcyclohexen-1-yl)-n-octylbenzene,
4-(4-ethylcyclohexen-1-yl)-n-octylbenzene,
4-(4-n-propylcyclohexen-1-yl)-n-octylbenzene,
4-(4-n-butylcyclohexen-1-yl)-n-octylbenzene,
4-(4-n-pentylcyclohexen-1-yl)-n-octylbenzene,
4-(4-n-hexylcyclohexen-1-yl)-n-octylbenzene,
4-(4-n-heptylcyclohexen-1-yl)-n-octylbenzene,
4-(4-n-octylcyclohexen-1-yl)-n-octylbenzene,
4-[4-(1-methylhexyl)-cyclohexen-1-yl]-n-octylbenzene,
4-[4-(2-methylbutyl)-cyclohexen-1-yl]-n-octylbenzene,
4-[4-(3-ethylpentyl)-cyclohexen-1-yl]-n-octylbenzene,
4-(4-methylcyclohexen-1-yl)-biphenyl,
4-(4-ethylcyclohexen-1-yl)-biphenyl,
4-(4-n-propylcyclohexen-1-yl)-biphenyl,
4-(4-n-butylcyclohexen-1-yl)-biphenyl,
4-(4-n-pentylcyclohexen-1-yl)-biphenyl,
4-(4-n-hexylcyclohexen-1-yl)-biphenyl,
4-(4-n-heptylcyclohexen-1-yl)-biphenyl,
4-(4-n-octylcyclohexen-1-yl)-biphenyl,
4-[4-(1-methylhexyl)-cyclohexen-1-yl]-biphenyl,
4-[4-(2-methylbutyl)-cyclohexen-1-yl]-biphenyl,
4-[4-(3-ethylpentyl)-cyclohexen-1-yl]-biphenyl,
4-(4-methylcyclohexen-1-yl)-4'-fluorobiphenyl,
4-(4-ethylcyclohexen-1-yl)-4'-fluorobiphenyl,
4-(4-n-propylcyclohexen-1-yl)-4'-fluorobiphenyl,
4-(4-n-butylcyclohexen-1-yl)-4'-fluorobiphenyl,
4-(4-n-pentylcyclohexen-1-yl)-4'-fluorobiphenyl,
4-(4-n-hexylcyclohexen-1-yl)-4'-fluorobiphenyl,
4-(4-n-heptylcyclohexen-1-yl)-4'-fluorobiphenyl,
4-(4-n-octylcyclohexen-1-yl)-4'-fluorobiphenyl,
4-[4-(1-methylhexyl)-cyclohexen-1-yl]-4'-fluorobiphenyl,
4-[4-(2-methylbutyl)-cyclohexen-1-yl]-4'-fluorobiphenyl,
4-[4-(3-ethylpentyl)-cyclohexen-1-yl]-4'-fluorobiphenyl, 4-(4-methylcyclohexen-1-yl)-4'-methoxybiphenyl,
4-(4-ethylcyclohexen-1-yl)-4'-methoxybiphenyl,
4-(4-n-propylcyclohexen-1-yl)-4'-methoxybiphenyl,
4-(4-n-butylcyclohexen-1-yl)-4'-methoxybiphenyl,
4-(4-n-pentylcyclohexen-1-yl)-4'-methoxybiphenyl,
4-(4-n-hexylcyclohexen-1-yl)-4'-methoxybiphenyl,
4-(4-n-heptylcyclohexen-1-yl)-4'-methoxybiphenyl,
4-(4-n-octylcyclohexen-1-yl)-4'-methoxybiphenyl,
4-[4-(1-methylhexyl)-cyclohexen-1-yl]-4'-methoxybiphenyl,
4-[4-(2-methylbutyl)-cyclohexen-1-yl]-4'-methoxybiphenyl,
4-[4-(3-ethylpentyl)-cyclohexen-1-yl]-4'-methoxybiphenyl, 4-(4-methylcyclohexen-1-yl)-4'-ethoxybiphenyl,
4-(4-ethylcyclohexen-1-yl)-4'-ethoxybiphenyl,
4-(4-n-propylcyclohexen-1-yl)-4'-ethoxybiphenyl,
4-(4-n-butylcyclohexen-1-yl)-4'-ethoxybiphenyl,
4-(4-n-pentylcyclohexen-1-yl)-4'-ethoxybiphenyl,
4-(4-n-hexylcyclohexen-1-yl)-4'-ethoxybiphenyl,
4-(4-n-heptylcyclohexen-1-yl)-4'-ethoxybiphenyl,
4-(4-n-octylcyclohexen-1-yl)-4'-ethoxybiphenyl,
4-[4-(1-methylhexyl)-cyclohexen-1-yl]-4'-ethoxybiphenyl,
4-[4-(2-methylbutyl)-cyclohexen-1-yl]-4'-ethoxybiphenyl,
4-[4-(3-ethylpentyl)-cyclohexen-1-yl]-4'-ethoxybiphenyl, 4-(4-methylcyclohexen-1-yl)-4'-n-propoxybiphenyl,
4-(4-ethylcyclohexen-1-yl)-4'-n-propoxybiphenyl,
4-(4-n-propylcyclohexen-1-yl)-4'-n-propoxybiphenyl,
4-(4-n-butylcyclohexen-1-yl)-4'-n-propoxybiphenyl,
4-(4-n-pentylcyclohexen-1-yl)-4'-n-propoxybiphenyl,
4-(4-n-hexylcyclohexen-1-yl)-4'-n-propoxybiphenyl,
4-(4-n-heptylcyclohexen-1-yl)-4'-n-propoxybiphenyl,
4-(4-n-octylcyclohexen-1-yl)-4'-n-propoxybiphenyl,
4-[4-(1-methylhexyl)-cyclohexen-1-yl]-4'-n-propoxybiphenyl,
4-[4-(2-methylbutyl)-cyclohexen-1-yl]-4'-n-propoxybiphenyl,
4-[4-(3-ethylpentyl)-cyclohexen-1-yl]-4'-n-propoxybiphenyl, 4-(4-methylcyclohexen-1-yl)-4'-n-butoxybiphenyl,
4-(4-ethylcyclohexen-1-yl)-4'-n-butoxybiphenyl,
4-(4-n-propylcyclohexen-1-yl)-4'-n-butoxybiphenyl,
4-(4-n-butylcyclohexen-1-yl)-4'-n-butoxybiphenyl,
4-(4-n-pentylcyclohexen-1-yl)-4'-n-butoxybiphenyl,
4-(4-n-hexylcyclohexen-1-yl)-4'-n-butoxybiphenyl,
4-(4-n-heptylcyclohexen-1-yl)-4'-n-butoxybiphenyl,
4-(4-n-octylcyclohexen-1-yl)-4'-n-butoxybiphenyl,
4-[4-(1-methylhexyl)-cyclohexen-1-yl]-4'-n-butoxybiphenyl,
4-[4-(2-methylbutyl)-cyclohexen-1-yl]-4'-n-butoxybiphenyl,
4-[4-(3-ethylpentyl)-cyclohexen-1-yl]-4'-n-butoxybiphenyl, 4-(4-methylcyclohexen-1-yl)-4'-n-pentyloxybiphenyl,
4-(4-ethylcyclohexen-1-yl)-4'-n-pentyloxybiphenyl,
4-(4-n-propylcyclohexen-1-yl)-4'-n-pentyloxybiphenyl,
4-(4-n-butylcyclohexen-1-yl)-4'-n-pentyloxybiphenyl,
4-(4-n-pentylcyclohexen-1-yl)-4'-n-pentyloxybiphenyl,
4-(4-n-hexylcyclohexen-1-yl)-4'-n-pentyloxybiphenyl,
4-(4-n-heptylcyclohexen-1-yl)-4'-n-pentyloxybiphenyl,
4-(4-n-octylcyclohexen-1-yl)-4'-n-pentyloxybiphenyl,
4-[4-(1-methylhexyl)-cyclohexen-1-yl]-4'-n-pentyloxybiphenyl,
4-[4-(2-methylbutyl)-cyclohexen-1-yl]-4'-n-pentyloxybiphenyl,
4-[4-(3-ethylpentyl)-cyclohexen-1-yl]-4'-n-pentyloxybiphenyl, 4-(4-methylcyclohexen-1-yl)-4'-n-hexyloxybiphenyl,
4-(4-ethylcyclohexen-1-yl)-4'-n-hexyloxybiphenyl,
4-(4-n-propylcyclohexen-1-yl)-4'-n-hexyloxybiphenyl,
4-(4-n-butylcyclohexen-1-yl)-4'-n-hexyloxybiphenyl,
4-(4-n-pentylcyclohexen-1-yl)-4'-n-hexyloxybiphenyl,
4-(4-n-hexylcyclohexen-1-yl)-4'-n-hexyloxybiphenyl,
4-(4-n-heptylcyclohexen-1-yl)-4'-n-hexyloxybiphenyl,
4-(4-n-octylcyclohexen-1-yl)-4'-n-hexyloxybiphenyl,
4-[4-(1-methylhexyl)-cyclohexen-1-yl]-4'-n-hexyloxybiphenyl,
4-[4-(2-methylbutyl)-cyclohexen-1-yl]-4'-n-hexyloxybiphenyl, 4-[4-(3-ethylpentyl)-cyclohexen-1-yl]-4'-n-hexyloxybiphenyl, 4-(4-methylcyclohexen-1-yl)-4'-n-heptyloxybiphenyl,
4-(4-ethylcyclohexen-1-yl)-B 4'-n-heptyloxybiphenyl,
4-(4-n-propylcyclohexen-1-yl)-4'-n-heptyloxybiphenyl,
4-(4-n-butylcyclohexen-1-yl)-4'-n-heptyloxybiphenyl,
4-(4-n-pentylcyclohexen-1-yl)-4'-n-heptyloxybiphenyl,
4-(4-n-hexylcyclohexen-1-yl)-4'-n-heptyloxybiphenyl,
4-(4-n-heptylcyclohexen-1-yl)-4'-n-heptyloxybiphenyl,
4-(4-n-octylcyclohexen-1-yl)-4'-n-heptyloxybiphenyl,
4-[4-(1-methylhexyl)-cyclohexen-1-tl]-4'-n-heptyloxybiphenyl,
4-[4-(2-methylbutyl)-cyclohexen-1-yl]-4'-n-heptyloxybiphenyl,
4-[4-(3-ethylpentyl)-cyclohexen-1-yl]-4'-n-heptyloxybiphenyl, 4-(4-methylcyclohexen-1-yl)-4'-n-octyloxybiphenyl,
4-(4-ethylcyclohexen-1-yl)-4'-n-octyloxybiphenyl,
4-(4-n-propylcyclohexen-1-yl)-4'-n-octyloxybiphenyl,
4-(4-n-butylcyclohexen-1-yl)-4'-n-octyloxybiphenyl,
4-(4-n-pentylcyclohexen-1-yl)-4'-n-octyloxybiphenyl,
4-(4-n-hexylcyclohexen-1-yl)-4'-n-octyloxybiphenyl,
4-(4-n-heptylcyclohexen-1-yl)-4'-n-octyloxybiphenyl,
4-(4-n-octylcyclohexen-1-yl)-4'-n-octyloxybiphenyl,
4-[4-(1-methylhexyl)-cyclohexen-1-yl]-4'-n-octyloxybiphenyl,
4-[4-(2-methylbutyl)-cyclohexen-1-yl]-4'-n-octyloxybiphenyl,
4-[4-(3-ethylpentyl)-cyclohexen-1-yl]-4'-n-octyloxybiphenyl, 4-(4-methylcyclohexen-1-yl)-4'-(1-methylbutoxy)-biphenyl,
4-(4-ethylcyclohexen-1-yl)-4'-(1-methylbutoxy)-biphenyl,
4-(4-n-propylcyclohexen-1-yl)-4'-(1-methylbutoxy)-biphenyl,
4-(4-n-butylcyclohexen-1-yl)-4'-(1-methylbutoxy)-biphenyl,
4-(4-n-pentylcyclohexen-1-yl)-4'-(1-methylbutoxy)-biphenyl,
4-(4-n-hexylcyclohexen-1-yl)-4'-(1-metylbutoxy)-biphenyl,
4-(4-n-heptylcyclohexen-1-yl)-4'-(1-methylbutoxy)-biphenyl,
4-(4-n-octylcyclohexen-1-yl)-4'-(1-methylbutoxy)-biphenyl, 4-(4-methylcyclohexen-1-yl)-4'-benzyloxybiphenyl,
4-(4-ethylcyclohexen-1-yl)-4'-benzyloxybiphenyl,
4-(4-n-propylcyclohexen-1-yl)-4'-benzyloxybiphenyl,
4-(4-n-butylcyclohexen-1-yl)-4'-benzyloxybiphenyl,
4-(4-n-pentylcyclohexen-1-yl)-4'-benzyloxybiphenyl,
4-(4-n-hexylcyclohexen-1-yl)-4'-benzyloxybiphenyl,
4-(4-n-heptylcyclohexen-1-yl)-4'-benzyloxybiphenyl,
4-(4-n-octylcyclohexen-1-yl)-4'-benzyloxybiphenyl,
4-[4-(1-methylhexyl)-cyclohexen-1-yl]-4'-benzyloxybiphenyl,
4-[4-(2-methylbutyl)-cyclohexen-1-yl]-4'-benzyloxybiphenyl,
4-[4-(3-ethylpentyl)-cyclohexen-1-yl]-4'-benzyloxybiphenyl, 4-(4-methylcyclohexen-1-yl)-4'-methylbiphenyl,
4-(4-ethylcyclohexen-1-yl)-4'-methylbiphenyl,
4-(4-n-propylcyclohexen-1-yl)-4'-methylbiphenyl,
4-(4-n-butylcyclohexen-1-yl)-4'-methylbiphenyl,
4-(4-n-pentylcyclohexen-1-yl)-4'-methylbiphenyl,
4-(4-n-hexylcyclohexen-1-yl)-4'-methylbiphenyl,
4-(4-n-heptylcyclohexen-1-yl)-4'-methylbiphenyl,
4-(4-n-octylcyclohexen-1-yl)-4'-methylbiphenyl,
4-[4-(1-methylhexyl)-cyclohexen-1-yl]-4'-methylbiphenyl,
4-[4-(2-methylbutyl)-cyclohexen-1-yl]-4'-methylbiphenyl,
4-[4-(3-ethylpentyl)-cyclohexen-1-yl]-4'-methylbiphenyl, 4-(4-methylcyclohexen-1-yl)-4'-ethylbiphenyl,
4-(4-ethylcyclohexen-1-yl)-4'-ethylbiphenyl,
4-(4-n-propylcyclohexen-1-yl)-4'-ethylbiphenyl,
4-(4-n-butylcyclohexen-1-yl)-4'-ethylbiphenyl,
4-(4-n-pentylcyclohexen-1-yl)-4'-ethylbiphenyl,
4-(4-n-hexylcyclohexen-1-yl)-4'-ethylbiphenyl,
4-(4-n-heptylcyclohexen-1-yl)-4'-ethylbiphenyl,
4-(4-n-octylcyclohexen-1-yl)-4'-ethylbiphenyl,
4-[4-(1-methylhexyl)-cyclohexen-1-yl]-4'-ethylbiphenyl,
4-[4-(2-methylbutyl)-cyclohexen-1-yl]-4'-ethylbiphenyl,
4-[4-(3-ethylpentyl)-cyclohexen-1-yl]-4'-ethylbiphenyl, 4-(4-methylcyclohexen-1-yl)-4'-n-propylbiphenyl,
4-(4-ethylcyclohexen-1-yl)-4'-n-propylbiphenyl,
4-(4-n-propylcyclohexen-1-yl)-4'-n-propylbiphenyl,
4-(4-n-butylcyclohexen-1-yl)-4'-n-propylbiphenyl,
4-(4-n-pentylcyclohexen-1-yl)-4'-n-propylbiphenyl,
4-(4-n-hexylcyclohexen-1-yl)-4'-n-propylbiphenyl,
4-(4-n-heptylcyclohexen-1-yl)-4'-n-propylbiphenyl,
4-(4-n-octylcyclohexen-1-yl)-4'-n-propylbiphenyl,
4-[4-(1-methylhexyl)-cyclohexen-1-yl]-4'-n-propylbiphenyl,
4-[4-(2-methylbutyl)-cyclohexen-1-yl]-4'-n-propylbiphenyl,
4-[4-(3-ethylpentyl)-cyclohexen-1-yl]-4'-n-propylbiphenyl, 4-(4-methylcyclohexen-1-yl)-4'-n-butylbiphenyl,
4-(4-ethylcyclohexen-1-yl)-4'-n-butylbiphenyl,
4-(4-n-propylcyclohexen-1-yl)-4'-n-butylbiphenyl,
4-(4-n-butylcyclohexen-1-yl)-4'-n-butylbiphenyl,
4-(4-n-pentylcyclohexen-1-yl)-4'-n-butylbiphenyl,
4-(4-n-hexylcyclohexen-1-yl)-4'-n-butylbiphenyl,
4-(4-n-heptylcyclohexen-1-yl)-4'-n-butylbiphenyl,
4-(4-n-octylcyclohexen-1-yl)-4'-n-butylbiphenyl,
4-[4-(1-methylhexyl)-cyclohexen-1-yl]-4'-n-butylbiphenyl,
4-[4-(2-methylbutyl)-cyclohexen-1-yl]-4'-n-butylbiphenyl,
4-[4-(3-ethylpentyl)-cyclohexen-1-yl]-4'-n-butylbiphenyl, 4-(4-methylcyclohexen-1-yl)-4'-n-pentylbiphenyl,
4-(4-ethylcyclohexen-1-yl)-4'-n-pentylbiphenyl,
4-(4-n-propylcyclohexen-1-yl)-4'-n-pentylbiphenyl,
4-(4-n-butylcyclohexen-1-yl)-4'-n-pentylbiphenyl,
4-(4-n-pentylcyclohexen-1-yl)-4'-n-pentylbiphenyl,
4-(4-n-hexylcyclohexen-1-yl)-4'-n-pentylbiphenyl,
4-(4-n-heptylcyclohexen-1-yl)-4'-n-pentylbiphenyl,
4-(4-n-octylcyclohexen-1-yl)-4'-n-pentylbiphenyl,
4-[4-(1-methylhexyl)-cyclohexen-1-yl]-4'-n-pentylbiphenyl,
4-[4-(2-methylbutyl)-cyclohexen-1-yl]-4'-n-pentylbiphenyl, 4-[4-(3-ethylpentyl)-cyclohexen-1-yl]-4'-n-pentylbiphenyl, 4-(4-methylcyclohexen-1-yl)-4'-(3-methylbutyl)-biphenyl,
4-(4-ethylcyclohexen-1-yl)-4'-(3-methylbutyl)-biphenyl,
4-(4-n-propylcyclohexen-1-yl)-4'-(3-methylbutyl)-biphenyl,
4-(4-n-butylcyclohexen-1-yl)-4'-(3-methylbutyl)-biphenyl,
4-(4-n-pentylcyclohexen-1-yl)-4'-(3-methylbutyl)-biphenyl,
4-(4-n-hexylcyclohexen-1-yl)-4'-(3-methylbutyl)-biphenyl,
4-(4-n-heptylcyclohexen-1-yl)-4'-(3-methylbutyl)-biphenyl,
4-(4-n-octylcyclohexen-1-yl)-4'-(3-methylbutyl)-biphenyl, 4-(4-methylcyclohexen-1-yl)-4'-n-hexylbiphenyl,
4-(4-ethylcyclohexen-1-yl)-4'-n-hexylbiphenyl,
4-(4-n-propylcyclohexen-1-yl)-4'-n-hexylbiphenyl,
4-(4-n-butylcyclohexen-1-yl)-4'-n-hexylbiphenyl,
4-(4-n-pentylcyclohexen-1-yl)-4'-n-hexylbiphenyl,
4-(4-n-hexylcyclohexen-1-yl)-4'-n-hexylbiphenyl,
4-(4-n-heptylcyclohexen-1-yl)-4'-n-hexylbiphenyl,
4-(4-n-octylcyclohexen-1-yl)-4'-n-hexylbiphenyl,
4-[4-(1-methylhexyl)-cyclohexen-1-yl]-4'-n-hexylbiphenyl,
4-[4-(2-methylbutyl)-cyclohexen-1-yl]-4'-n-hexylbiphenyl,
4-[4-(3-ethylpentyl)-cyclohexen-1-yl]-4'-n-hexylbiphenyl, 4-(4-methylcyclohexen-1-yl)-4'-(1-methylpentyl)-biphenyl,
4-(4-ethylcyclohexen-1-yl)-4'-(1-methylpentyl)-biphenyl,
4-(4-n-propylcyclohexen-1-yl)-4'-(1-methylpentyl)-biphenyl,
4-(4-n-butylcyclohexen-1-yl)-4'-(1-methylpentyl)-biphenyl,
4-(4-n-pentylcyclohexen-1-yl)-4'-(1-methylpentyl)-biphenyl,
4-(4-n-hexylcyclohexen-1-yl)-4'-(1-methylpentyl)-biphenyl,
4-(4-n-heptylcyclohexen-1-yl)-4'-(1-methylpentyl)-biphenyl,
4-(4-n-octylcyclohexen-1-yl)-4'-(1-methylpentyl)-biphenyl 4-(4-methylcyclohexen-1-yl)-4'-n-heptylbiphenyl,
4-(4-ethylcyclohexen-1-yl)-4'-n-heptylbiphenyl,
4-(4-n-propylcyclohexen-1-yl)-4'-n-heptylbiphenyl,
4-(4-n-butylcyclohexen-1-yl)-4'-n-heptylbiphenyl,
4-(4-n-pentylcyclohexen-1-yl)-4'-n-heptylbiphenyl,
4-(4-n-hexylcyclohexen-1-yl)-4'-n-heptylbiphenyl,
4-(4-n-heptylcyclohexen-1-yl)-4'-n-heptylbiphenyl,
4-(4-n-octylcyclohexen-1-yl)-4'-n-heptylbiphenyl,
4-[4-(1-methylhexyl)-cyclohexen-1-yl]-4'-n-heptylbiphenyl,
4-[4-(2-methylbutyl)-cyclohexen-1-yl]-4'-n-heptylbiphenyl,
4-[4-(3-ethylpentyl)-cyclohexen-1-yl]-4'-n-heptylbiphenyl, 4-(4-methylcyclohexen-1-yl)-4'-n-octylbiphenyl,
4-(4-ethylcyclohexen-1-yl)-4'-n-octylbiphenyl,
4-(4-n-propylcyclohexen-1-yl)-4'-n-octylbiphenyl,
4-(4-n-butylcyclohexen-1-yl)-4'-n-octylbiphenyl,
4-(4-n-pentylcyclohexen-1-yl)-4'-n-octylbiphenyl,
4-(4-n-hexylcyclohexen-1-yl)-4'-n-octylbiphenyl,
4-(4-n-heptylcyclohexen-1-yl)-4'-n-octylbiphenyl,
4-(4-n-octylcyclohexen-1-yl)-4'-n-octylbiphenyl,
4-[4-(1-methylhexyl)-cyclohexen-1-yl]-4'-n-octylbiphenyl,
4-[4-(2-methylbutyl)-cyclohexen-1-yl]-4'-n-octylbiphenyl and
4-[4-(3-ethylpentyl)-cyclohexen-1-yl]-4'-n-octylbiphenyl.

EXAMPLE 3

(a) A mixture of 33 g of 4-(4-n-pentylcyclohexen-1-yl)-benzyloxybenzene and 35 g of pyridine hydrochloride is heated in an oilbath to 200° for 1 hour. After cooling, the reaction mixture is poured into 1,000 ml of water and the suspension obtained is extracted three times with 400 ml of diethyl ether. The combined extracts are dried over sodium sulphate and evaporated, finally under reduced pressure. The 4-(4-n-pentylcyclohexen-1-yl)-phenol which remains is recrystallized from methanol; yield 16 g of colorless crystals, m.p. 15°.

The following are prepared analogously:
4-(4-methylcyclohexen-1-yl)-phenol,
4-(4-ethylcyclohexen-1-yl)-phenol,
4-(4-n-propylcyclohexen-1-yl)-phenol,
4-(4-n-butylcyclohexen-1-yl)-phenol,
4-(4-n-hexylcyclohexen-1-yl)-phenol,
4-(4-n-heptylcyclohexen-1-yl)-phenol,
4-(4-n-octylcyclohexen-1-yl)-phenol,
4-[4-(1-methylhexyl)-cyclohexen-1-yl]-phenol,
4-[4-(2-methylbutyl)-cyclohexen-1-yl]-phenol,
4-[4-(3-ethylpentyl)-cyclohexen-1-yl]-phenol, 4-(4-methylcyclohexen-1-yl)-4'-hydroxybiphenyl,
4-(4-ethylcyclohexen-1-yl)-4'-hydroxybiphenyl,
4-(4-n-propylcyclohexen-1-yl)-4'-hydroxybiphenyl,
4-(4-n-butylcyclohexen-1-yl)-4'-hydroxybiphenyl,
4-(4-n-pentylcyclohexen-1-yl)-4'-hydroxybiphenyl,
4-(4-n-hexylcyclohexen-1-yl)-4'-hydroxybiphenyl,
4-(4-n-heptylcyclohexen-1-yl)-4'-hydroxybiphenyl,
4-(4-n-octylcyclohexen-1-yl)-4'-hydroxybiphenyl,
4-[4-(1-methylhexyl)-cyclohexen-1-yl]-4'-hydroxybiphenyl,
4-[4-(2-methylbutyl)-cyclohexen-1-yl]-4'-hydroxybiphenyl and
4-[4-(3-ethylpentyl)-cyclohexen-1-yl]-4'-hydroxybiphenyl.

(b) 2.5 g of n-butyryl chloride is added dropwise with stirring at 100° to a solution of 6 g of 4-(4-n-pentylcyclohexen-1-yl)-phenol and 2 g of pyridine in 250 ml of toluene. The reaction mixture is stirred for another 2 hours at 100° and then filtered, and the filtrate is evaporated. The 4-(4-n-pentylcyclohexen-1-yl)-n-butyryloxybenzene which remains is recrystallized from ethanol; yield 4.6 g of colorless crystals, m.p. 22°, c.p. 38°.

The following are prepared analogously:
4-(4-methylcyclohexen-1-yl)-acetoxybenzene,
4-(4-ethylcyclohexen-1-yl)-acetoxybenzene,
4-(4-n-propylcyclohexen-1-yl)-acetoxybenzene,
4-(4-n-butylcyclohexen-1-yl)-acetoxybenzene,
4-(4-n-pentylcyclohexen-1-yl)-acetoxybenzene,
4-(4-n-hexylcyclohexen-1-yl)-acetoxybenzene,
4-(4-n-heptylcyclohexen-1-yl)-acetoxybenzene, 4-(4-n-octylcyclohexen-1-yl)-acetoxybenzene,
4-[4-(1-methylhexyl)-cyclohexen-1-yl]-acetoxybenzene,
4-[4-(2-methylbutyl)-cyclohexen-1-yl]-acetoxybenzene,
4-[4-(3-ethylpentyl)-cyclohexen-1-yl]-acetoxybenzene, 4-(4-methylcyclohexen-1-yl)-propionyloxybenzene,
4-(4-ethylcyclohexen-1-yl)-propionyloxybenzene,
4-(4-n-propylcyclohexen-1-yl)-propionyloxybenzene,
4-(4-n-butylcyclohexen-1-yl)-propionyloxybenzene,
4-(4-n-pentylcyclohexen-1-yl)-propionyloxybenzene,
4-(4-n-hexylcyclohexen-1-yl)-propionyloxybenzene,
4-(4-n-heptylcyclohexen-1-yl)-propionyloxybenzene,
4-(4-n-octylcyclohexen-1-yl)-propionyloxybenzene,
4-[4-(1-methylhexyl)-cyclohexen-1-yl]-propionyloxybenzene,
4-[4-(2-methylbutyl)-cyclohexen-1-yl]-propionyloxybenzene,
4-[4-(3-ethylpentyl)-cyclohexen-1-yl]-propionyloxybenzene, 4-(4-methylcyclohexen-1-yl)-n-butyryloxybenzene,
4-(4-ethylcyclohexen-1-yl)-n-butyryloxybenzene,
4-(4-n-propylcyclohexen-1-yl)-n-butyryloxybenzene,
4-(4-n-butylcyclohexen-1-yl)-n-butyryloxybenzene,
4-(4-n-hexylcyclohexen-1-yl)-n-butyryloxybenzene,
4-(4-n-heptylcyclohexen-1-yl)-n-butyryloxybenzene,
4-(4-n-octylcyclohexen-1-yl)-n-butyryloxybenzene,
4-[4-(1-methylhexyl)-cyclohexen-1-yl]-n-butyryloxybenzene,
4-[4-(2-methylbutyl)-cyclohexen-1-yl]-n-butyryloxybenzene,
4-[4-(3-ethylpentyl)-cyclohexen-1-yl]-n-butyryloxybenzene, 4-(4-methylcyclohexen-1-yl)-n-pentanoyloxybenzene,
4-(4-ethylcyclohexen-1-yl)-n-pentanoyloxybenzene,
4-(4-n-propylcyclohexen-1-yl)-n-pentanoyloxybenzene,
4-(4-n-butylcyclohexen-1-yl)-n-pentanoyloxybenzene,
4-(4-n-pentylcyclohexen-1-yl)-n-pentanoyloxybenzene,
4-(4-n-hexylcyclohexen-1-yl)-n-pentanoyloxybenzene,
4-(4-n-heptylcyclohexen-1-yl)-n-pentanoyloxybenzene,
4-(4-n-octylcyclohexen-1-yl)-n-pentanoyloxybenzene,
4-[4-(1-methylhexyl)-cyclohexen-1-yl]-n-pentanoyloxybenzene,
4-[4-(2-methylbutyl)-cyclohexen-1-yl]-n-pentanoyloxybenzene,
4-[4-(3-ethylpentyl)-cyclohexen-1-yl]-n-pentanoyloxybenzene, 4-(4-methylcyclohexen-1-yl)-n-hexanoyloxybenzene,
4-(4-ethylcyclohexen-1-yl)-n-hexanoyloxybenzene,
4-(4-n-propylcyclohexen-1-yl)-n-hexanoyloxybenzene,
4-(4-n-butylcyclohexen-1-yl)-n-hexanoyloxybenzene,
4-(4-n-pentylcyclohexen-1-yl)-n-hexanoyloxybenzene,
4-(4-n-hexylcyclohexen-1-yl)-n-hexanoyloxybenzene,
4-(4-n-heptylcyclohexen-1-yl)-n-hexanoyloxybenzene,
4-(4-n-octylcyclohexen-1-yl)-n-hexanoyloxybenzene,
4-[4-(1-methylhexyl)-cyclohexen-1-yl]-n-hexanoyloxybenzene,
4-[4-(2-methylbutyl)-cyclohexen-1-yl]-n-hexanoyloxybenzene,
4-[4-(3-ethylpentyl)-cyclohexen-1-yl]-n-hexanoyloxybenzene, 4-(4-methylcyclohexen-1-yl)-n-heptanoyloxybenzene,
4-(4-ethylcyclohexen-1-yl)-n-heptanoyloxybenzene,
4-(4-n-propylcyclohexen-1-yl)-n-heptanoyloxybenzene,
4-(4-n-butylcyclohexen-1-yl)-n-heptanoyloxybenzene,
4-(4-n-pentylcyclohexen-1-yl)-n-heptanoyloxybenzene,
4-(4-n-hexylcyclohexen-1-yl)-n-heptanoyloxybenzene,
4-(4-n-heptylcyclohexen-1-yl)-n-heptanoyloxybenzene,
4-(4-n-octylcyclohexen-1-yl)-n-heptanoyloxybenzene,
4-[4-(1-methylhexyl)-cyclohexen-1-yl]-n-heptanoyloxybenzene,
4-[4-(2-methylbutyl)-cyclohexen-1-yl]-n-heptanoyloxybenzene,
4-[4-(3-ethylpentyl)-cyclohexen-1-yl]-n-heptanoyloxybenzene, 4-(4-methylcyclohexen-1-yl)-n-octanoyloxybenzene,
4-(4-ethylcyclohexen-1-yl)-n-octanoyloxybenzene,
4-(4-n-propylcyclohexen-1-yl)-n-octanoyloxybenzene,
4-(4-n-butylcyclohexen-1-yl)-n-octanoyloxybenzene,
4-(4-n-pentylcyclohexen-1-yl)-n-octanoyloxybenzene,
4-(4-n-hexylcyclohexen-1-yl)-n-octanoyloxybenzene,
4-(4-n-heptylcyclohexen-1-yl)-n-octanoyloxybenzene,
4-(4-n-octylcyclohexen-1-yl)-n-octanoyloxybenzene,
4-[4-(1-methylhexyl)-cyclohexen-1-yl]-n-octanoyloxybenzene,
4-[4-(2-methylbutyl)-cyclohexen-1-yl]-n-octanoyloxybenzene,
4-[4-(3-ethylpentyl)-cyclohexen-1-yl]-n-octanoyloxybenzene, 4-(4-methylcyclohexen-1-yl)-n-nonanoyloxybenzene,
4-(4-ethylcyclohexen-1-yl)-n-nonanoyloxybenzene,
4-(4-n-propylcyclohexen-1-yl)-n-nonanoyloxybenzene,
4-(4-n-butylcyclohexen-1-yl)-n-nonanoyloxybenzene,
4-(4-n-pentylcyclohexen-1-yl)-n-nonanoyloxybenzene,
4-(4-n-hexylcyclohexen-1-yl)-n-nonanoyloxybenzene,
4-[4-(1-methylhexyl)-cyclohexen-1-yl]-n-nonanoyloxybenzene,
4-[4-(2-methylbutyl)-cyclohexen-1-yl]-n-nonanoyloxybenzene,
4-[4-(3-ethylpentyl)-cyclohexen-1-yl]-n-nonanoyloxybenzene, 4-(4-methylcyclohexen-1-yl)-ethoxycarbonyloxybenzene,
4-(4-ethylcyclohexen-1-yl)-ethoxycarbonyloxybenzene,
4-(4-n-propylcyclohexen-1-yl)-ethoxycarbonyloxybenzene,
4-(4-n-butylcyclohexen-1-yl)-ethoxycarbonyloxybenzene,
4-(4-n-pentylcyclohexen-1-yl)-ethoxycarbonyloxybenzene,
4-(4-n-hexylcyclohexen-1-yl)-ethoxycarbonyloxybenzene,
4-(4-n-heptylcyclohexen-1-yl)-ethoxycarbonyloxybenzene,
4-(4-n-octylcyclohexen-1-yl)-ethoxycarbonyloxybenzene,
4-[4-(1-methylhexyl)-cyclohexen-1-yl]-ethoxycarbonyloxybenzene,
4-[4-(2-methylbutyl)-cyclohexen-1-yl]-ethoxycarbonyloxybenzene,
4-[4-(3-ethylpentyl)-cyclohexen-1-yl]-ethoxycarbonyloxybenzene, 4-(4-methylcyclohexen-1-yl)-n-butoxycarbonyloxybenzene,
4-(4-ethylcyclohexen-1-yl)-n-butoxycarbonyloxybenzene,
4-(4-n-propylcyclohexen-1-yl)-n-butoxycarbonyloxybenzene, 4-(4-n-butylcyclohexen-1-yl)-n-butoxycarbonyloxybenzene,
4-(4-n-pentylcyclohexen-1-yl)-n-butoxycarbonyloxybenzene,
4-(4-n-hexylcyclohexen-1-yl)-n-butoxycarbonyloxybenzene,
4-(4-n-heptylcyclohexen-1-yl)-n-butoxycarbonyloxybenzene,
4-(4-n-octylcyclohexen-1-yl)-n-butoxycarbonyloxybenzene,
4-[4-(1-methylhexyl)-cyclohexen-1-yl]-n-butoxycarbonyloxybenzene,
4-[4-(2-methylbutyl)-cyclohexen-1-yl]-n-butoxycarbonyloxybenzene,
4-[4-(3-ethylpentyl)-cyclohexen-1-yl]-n-butoxycarbonyloxybenzene, 4-(4-methylcyclohexen-1-yl)-4'-acetoxy-biphenyl,
4-(4-ethylcyclohexen-1-yl)-4'-acetoxy-biphenyl,
4-(4-n-propylcyclohexen-1-yl)-4'-acetoxy-biphenyl,
4-(4-n-butylcyclohexen-1-yl)-4'-acetoxy-biphenyl,
4-(4-n-pentylcyclohexen-1-yl)-4'-acetoxy-biphenyl,
4-(4-n-hexylcyclohexen-1-yl)-4'-acetoxy-biphenyl,
4-(4-n-heptylcyclohexen-1-yl)-4'-acetoxy-biphenyl,
4-(4-n-octylcyclohexen-1-yl)-4'-acetoxy-biphenyl,
4-[4-(1-methylhexyl)-cyclohexen-1-yl]-4'-acetoxy-biphenyl,
4-[4-(2-methylbutyl)-cyclohexen-1-yl]-4'-acetoxy-biphenyl,
4-[4-(3-ethylpentyl)-cyclohexen-1-yl]-4'-acetoxy-biphenyl, 4-(4-methylcyclohexen-1-yl)-4'-propionyloxy-biphenyl,
4-(4-ethylcyclohexen-1-yl)-4'-propionyloxy-biphenyl,
4-(4-n-propylcyclohexen-1-yl)-4'-propionyloxy-biphenyl,
4-(4-n-butylcyclohexen-1-yl)-4'-propionyloxy-biphenyl,
4-(4-n-pentylcyclohexen-1-yl)-4'-propionyloxy-biphenyl,
4-(4-n-hexylcyclohexen-1-yl)-4'-propionyloxy-biphenyl,
4-(4-n-heptylcyclohexen-1-yl)-4'-propionyloxy-biphenyl,
4-(4-n-octylcyclohexen-1-yl)-4'-propionyloxy-biphenyl,
4-[4-(1-methylhexyl)-cyclohexen-1-yl]-4'-propionyloxy-biphenyl,
4-[4-(2-methylbutyl)-cyclohexen-1-yl]-4'-propionyloxy-biphenyl,
4-[4-(3-ethylpentyl)-cyclohexen-1-yl]-4'-propionyloxy-biphenyl, 4-(4-methylcyclohexen-1-yl)-4'-n-butyryloxy-biphenyl,
4-(4-ethylcyclohexen-1-yl)-4'-n-butyryloxy-biphenyl,
4-(4-n-propylcyclohexen-1-yl)-4'-n-butyryloxy-biphenyl,
4-(4-n-butylcyclohexen-1-yl)-4'-n-butyryloxy-biphenyl,
4-(4-n-pentylcyclohexen-1-yl)-4'-n-butyryloxy-biphenyl,
4-(4-n-hexylcyclohexen-1-yl)-4'-n-butyryloxy-biphenyl,
4-(4-n-heptylcyclohexen-1-yl)-4'-n-butyryloxy-biphenyl,
4-(4-n-octylcyclohexen-1-yl)-4'-n-butyryloxy-biphenyl,
4-[4-(1-methylhexyl)-cyclohexen-1-yl]-4'-n-butyryloxy-biphenyl,
4-[4-(2-methylbutyl)-cyclohexen-1-yl]-4'-n-butyryloxy-biphenyl,
4-[4-(3-ethylpentyl)-cyclohexen-1-yl]-4'-n-butyryloxy-biphenyl, 4-(4-methylcyclohexen-1-yl)-4'-n-pentanoyloxy-biphenyl,
4-(4-ethylcyclohexen-1-yl)-4'-n-pentanoyloxy-biphenyl,
4-(4-n-propylcyclohexen-1-yl)-4'-n-pentanoyloxy-biphenyl,
4-(4-n-butylcyclohexen-1-yl)-4'-n-pentanoyloxy-biphenyl,
4-(4-n-pentylcyclohexen-1-yl)-4'-n-pentanoyloxy-biphenyl,
4-(4-n-hexylcyclohexen-1-yl)-4'-n-pentanoyloxy-biphenyl,
4-(4-n-heptylcyclohexen-1-yl)-4'-n-pentanoyloxy-biphenyl,
4-(4-n-octylcyclohexen-1-yl)-4'-n-pentanoyloxy-biphenyl,
4-[4-(1-methylhexyl)-cyclohexen-1-yl]-4'-n-pentanoyloxy-biphenyl,
4-[4-(2-methylbutyl)-cyclohexen-1-yl]-4'-n-pentanoyloxy-biphenyl,
4-[4-(3-ethylpentyl)-cyclohexen-1-yl]-4'-n-pentanoyloxy-biphenyl, 4-(4-methylcyclohexen-1-yl)-4'-n-hexanoyloxy-biphenyl,
4-(4-ethylcyclohexen-1-yl)-4'-n-hexanoyloxy-biphenyl,
4-(4-n-propylcyclohexen-1-yl)-4'-n-hexanoyloxy-biphenyl,
4-(4-n-butylcyclohexen-1-yl)-4'-n-hexanoyloxy-biphenyl,
4-(4-n-pentylcyclohexen-1-yl)-4'-n-hexanoyloxy-biphenyl,
4-(4-n-hexylcyclohexen-1-yl)-4'-n-hexanoyloxy-biphenyl,
4-(4-n-heptylcyclohexen-1-yl)-4'-n-hexanoyloxy-biphenyl,
4-(4-n-octylcyclohexen-1-yl)-4'-n-hexanoyloxy-biphenyl,
4-[4-(1-methylhexyl)-cyclohexen-1-yl]-4'-n-hexanoyloxy-biphenyl,
4-[4-(2-methylbutyl)-cyclohexen-1-yl]-4'-n-hexanoyloxy-biphenyl,
4-[4-(3-ethylpentyl)-cyclohexen-1-yl]-4'-n-hexanoyloxy-biphenyl, 4-(4-methylcyclohexen-1-yl)-4'-n-heptanoyloxy-biphenyl,
4-(4-ethylcyclohexen-1-yl)-4'-n-heptanoyloxy-biphenyl,
4-(4-n-propylcyclohexen-1-yl)-4'-n-heptanoyloxy-biphenyl,
4-(4-n-butylcyclohexen-1-yl)-4'-n-heptanoyloxy-biphenyl,
4-(4-n-pentylcyclohexen-1-yl)-4'-n-heptanoyloxy-biphenyl,
4-(4-n-hexylcyclohexen-1-yl)-4'-n-heptanoyloxy-biphenyl,
4-(4-n-heptylcyclohexen-1-yl)-4'-n-heptanoyloxy-biphenyl,
4-(4-n-octylcyclohexen-1-yl)-4'-n-heptanoyloxy-biphenyl,
4-[4-(1-methylhexyl)-cyclohexen-1-yl]-4'-n-heptanoyloxy-biphenyl,
4-[4-(2-methylbutyl)-cyclohexen-1-yl]-4'-n-heptanoyloxy-biphenyl,
4-[4-(3-ethylpentyl)-cyclohexen-1-yl]-4'-n-heptanoyloxy-biphenyl, 4-(4-methylcyclohexen-1-yl)-4'-n-octanoyloxy-biphenyl,
4-(4-ethylcyclohexen-1-yl)-4'-n-octanoyloxy-biphenyl,
4-(4-n-propylcyclohexen-1-yl)-4'-n-octanoyloxy-biphenyl,
4-(4-n-butylcyclohexen-1-yl)-4'-n-octanoyloxy-biphenyl,
4-(4-n-pentylcyclohexen-1-yl)-4'-n-octanoyloxy-biphenyl,
4-(4-n-hexylcyclohexen-1-yl)-4'-n-octanoyloxy-biphenyl,
4-(4-n-heptylcyclohexen-1-yl)-4'-n-octanoyloxy-biphenyl,
4-(4-n-octylcyclohexen-1-yl)-4'-n-octanoyloxy-biphenyl,
4-[4-(1-methylhexyl)-cyclohexen-1-yl]-4'-n-octanoyloxy-biphenyl,
4-[4-(2-methylbutyl)-cyclohexen-1-yl]-4'-n-octanoyloxy-biphenyl,
4-[4-(3-ethylpentyl)-cyclohexen-1-yl]-4'-n-octanoyloxy-biphenyl, 4-(4-methylcyclohexen-1-yl)-4'-n-nonanoyloxy-biphenyl,
4-(4-ethylcyclohexen-1-yl)-4'-n-nonanoyloxy-biphenyl,
4-(4-n-propylcyclohexen-1-yl)-4'-n-nonanoyloxy-biphenyl,
4-(4-n-butylcyclohexen-1-yl)-4'-n-nonanoyloxy-biphenyl,
4-(4-n-pentylcyclohexen-1-yl)-4'-n-nonanoyloxy-biphenyl,
4-(4-n-hexylcyclohexen-1-yl)-4'-n-nonanoyloxy-biphenyl,
4-[4-(1-methylhexyl)-cyclohexen-1-yl]-4'-n-nonanoyloxy-biphenyl,
4-[4-(2-methylbutyl)-cyclohexen-1-yl]-4'-n-nonanoyloxy-biphenyl,
4-[4-(3-ethylpentyl)-cyclohexen-1-yl]-4'-n-nonanoyloxy-biphenyl, 4-(4-methylcyclohexen-1-yl)-4'-methoxycarbonyloxy-biphenyl,
4-(4-ethylcyclohexen-1-yl)-4'-methoxycarbonyloxy-biphenyl,
4-(4-n-propylcyclohexen-1-yl)-4'-methoxycarbonyloxy-biphenyl,
4-(4-n-butylcyclohexen-1-yl)-4'-methoxycarbonyloxy-biphenyl,
4-(4-n-pentylcyclohexen-1-yl)-4'-methoxycarbonyloxy-biphenyl,
4-(4-n-hexylcyclohexen-1-yl)-4'-methoxycarbonyloxy-biphenyl,
4-(4-n-heptylcyclohexen-1-yl)-4'-methoxycarbonyloxy-biphenyl,
4-(4-n-octylcyclohexen-1-yl)-4'-methoxycarbonyloxy-biphenyl,
4-[4-(1-methylhexyl)-cyclohexen-1-yl]-4'-methoxycarbonyloxy-biphenyl,
4-[4-(2-methylbutyl)-cyclohexen-1-yl]-4'-methoxycarbonyloxy-biphenyl,
4-[4-(3-ethylpentyl)-cyclohexen-1-yl]-4'-methoxycarbonyloxy-biphenyl, 4-(4-methylcyclohexen-1-yl)-4'-n-butoxycarbonyloxy-biphenyl,
4-(4-ethylcyclohexen-1-yl)-4'-n-butoxycarbonyloxy-biphenyl,
4-(4-n-propylcyclohexen-1-yl)-4'-n-butoxycarbonyloxy-biphenyl,
4-(4-n-butylcyclohexen-1-yl)-4'-n-butoxycarbonyloxy-biphenyl,
4-(4-n-pentycyclohexen-1-yl)-4'-n-butoxycarbonyloxy-biphenyl,
4-(4-n-hexylcyclohexen-1-yl)-4'-n-butoxycarbonyloxy-biphenyl,
4-(4-n-heptylcyclohexen-1-yl)-4'-n-butoxycarbonyloxy-biphenyl,
4-(4-n-octylcyclohexen-1-yl)-4'-n-butoxycarbonyloxy-biphenyl,
4-[4-(1-methylhexyl)-cyclohexen-1-yl]-4'-n-butoxycarbonyloxy-biphenyl,
4-[4-(2-methylbutyl)-cyclohexen-1-yl]-4'-n-butoxycarbonyloxy-biphenyl and
4-[4-(3-ethylpentyl)-cyclohexen-1-yl]-4'-n-butoxycarbonyloxy-biphenyl.

EXAMPLE 4

(a) A solution of 50 g of 2-(4-bromophenyl)-4,4-dimethyl-2-oxazoline in 600 ml of tetrahydrofuran is added dropwise to a boiling suspension of 6 g of magnesium in 100 ml of tetrahydrofuran and the reaction mixture is subsequently heated to the boil for another 2 hours. A solution of 2.8 g of 4-n-propylcyclohexanone in 50 ml of tetrahydrofuran is then added dropwise and the reaction mixture is heated to the boil for 4 hours with stirring. After cooling, 500 ml of 10% strength aqueous ammonium chloride solution is added to the reaction mixture which is then extracted three times with 600 ml of diethyl ether. The combined extracts are dried over sodium sulphate and evaporated. The residue is dissolved in 120 ml of ethanol and, after the addition of 2 ml of concentrated sulphuric acid, the solution is heated to the boil for 16 hours. Subsequently, the reaction mixture is concentrated to 25 ml and subjected to chromatography on a neutral alumina column. 28 g of ethyl 4-(4-n-propylcyclohexen-1-yl)-benzoate is eluted with diethyl ether. This material is heated to the boil for 3 hours with 200 ml of 10% strength aqueous sodium hydroxide solution and 4-(4-n-propylcyclohexen-1-yl)-benzoic acid is isolated from the reaction mixture after acidification with dilute hydrochloric acid, extraction of the mixture with diethyl ether, drying of the extract and evaporation; yield 24 g of colorless crystals, m.p. 93°.

The following are prepared analogously:
4-(4-methylcyclohexen-1-yl)-benzoic acid,
4-(4-ethylcyclohexen-1-yl)-benzoic acid,
4-(4-n-butylcyclohexen-1-yl)-benzoic acid,
4-(4-n-pentylcyclohexen-1-yl)-benzoic acid,
4-(4-n-hexylcyclohexen-1-yl)-benzoic acid,
4-(4-n-heptylcyclohexen-1-yl)-benzoic acid,
4-(4-n-octylcyclohexen-1-yl)-benzoic acid,
4-[4-(1-methylhexyl)-cyclohexen-1-yl]-benzoic acid,
4-[4-(2-methylbutyl)-cyclohexen-1-yl]-benzoic acid,
4-[4-(3-ethylpentyl)-cyclohexen-1-yl]-benzoic acid, 4-(4-methylcyclohexen-1-yl)-4'-carboxybiphenyl,
4-(4-ethylcyclohexen-1-yl)-4'-carboxybiphenyl,
4-(4-n-propylcyclohexen-1-yl)-4'-carboxybiphenyl,
4-(4-n-butylcyclohexen-1-yl)-4'-carboxybiphenyl,
4-(4-n-pentylcyclohexen-1-yl)-4'-carboxybiphenyl,
4-(4-n-hexylcyclohexen-1-yl)-4'-carboxybiphenyl,
4-(4-n-heptylcyclohexen-1-yl)-4'-carboxybiphenyl,
4-(4-n-octylcyclohexen-1-yl)-4'-carboxybiphenyl, 4-[4-(1-methylhexyl)-cyclohexen-1-yl]-4'-carboxybiphenyl,
4-[4-(2-methylbutyl)-cyclohexen-1-yl]-4'-carboxybiphenyl and
4-[4-(3-ethylpentyl)-cyclohexen-1-yl]-4'-carboxybiphenyl.

(b) 5 g of 4-(4-n-propylcyclohexen-1-yl)-benzoic acid is heated to the boil for 8 hours with 50 ml of thionyl chloride and the excess thionyl chloride is distilled off. The residue is heated to 100° in a sealed tube with 4.2 g of phosphorus pentachloride for 24 hours. After cooling, the reaction mixture is poured into 100 ml of ice water and 50 ml of 2N sodium hydroxide solution is added to the mixture. The alkaline solution is extracted twice by shaking with 50 ml of methylene chloride, and the combined organic phases are washed with water, dried over calcium chloride and evaporated. Over the course of 20 minutes, 2.2 g of antimony trifluoride is added at 130° to the residue of 4-(4-n-propylcyclohexen-1-yl)-trichloromethyl-benzene. After an additional 5 minutes at 130°, the reaction mixture is allowed to cool and is poured into 40 ml of a mixture of equal parts of ice and 36% strength aqueous hydrochloric acid. The aqueous reaction mixture is extracted twice with 40 ml of diethyl ether, and the extracts are washed with 5% strength aqueous sodium bicarbonate solution and water, dried over sodium sulphate and evaporated. The 4-(4-n-propylcyclohexen-1-yl)-trifluoromethylbenzene which remains is recrystallized from methanol; yield 2.5 g of colorless crystals, m.p. 21°.

The following are prepared analogously:
4-(4-methylcyclohexen-1-yl)-trifluoromethyl-benzene,
4-(4-ethylcyclohexen-1-yl)-trifluoromethyl-benzene,
4-(4-n-butylcyclohexen-1-yl)-trifluoromethyl-benzene,
4-(4-n-pentylcyclohexen-1-yl)-trifluoromethyl-benzene,
4-(4-n-hexylcyclohexen-1-yl)-trifluoromethyl-benzene,
4-(4-n-heptylcyclohexen-1-yl)-trifluoromethyl-benzene,
4-(4-n-octylcyclohexen-1-yl)-trifluoromethyl-benzene,
4-[4-(1-methylhexyl)-cyclohexen-1-yl]-trifluoromethyl-benzene,
4-[4-(2-methylbutyl)-cyclohexen-1-yl]-trifluoromethyl-benzene,
4-[4-(3-ethylpentyl)-cyclohexen-1-yl]-trifluoromethyl-benzene, 4-(4-methylcyclohexen-1-yl)-4'-trifluoromethyl-biphenyl,
4-(4-ethylcyclohexen-1-yl)-4'-trifluoromethyl-biphenyl,
4-(4-n-propylcyclohexen-1-yl)-4'-trifluoromethyl-biphenyl,
4-(4-n-butylcyclohexen-1-yl)-4'-trifluoromethyl-biphenyl,
4-(4-n-pentylcyclohexen-1-yl)-4'-trifluoromethyl-biphenyl,
4-(4-n-hexylcyclohexen-1-yl)-4'-trifluoromethyl-biphenyl,
4-(4-n-heptylcyclohexen-1-yl)-4'-trifluoromethyl-biphenyl,
4-(4-n-octylcyclohexen-1-yl)-4'-trifluoromethyl-biphenyl,
4-[4-(1-methylhexyl)-cyclohexen-1-yl]-4'-trifluoromethyl-biphenyl,
4-[4-(2-methylbutyl)-cyclohexen-1-yl]-4'-trifluoromethyl-biphenyl and
4-[4-(3-ethylpentyl)-cyclohexen-1-yl]-4'-trifluoromethyl-biphenyl.

EXAMPLE 5

12 g of 4-(4-n-propylcyclohexen-1-yl)-benzoic acid and 70 g of thionyl chloride are heated to the boil for 8 hours and the excess thionyl chloride is then distilled off. The residue is dissolved in 100 ml of toluene and this solution is added dropwise, at 85°, to a solution of 6.5 g of 4-n-propylphenol and 4 g of pyridine in 200 ml of toluene. The reaction mixture is heated to the boil for 16 hours with stirring. After cooling, the pyridine hydrochloride which has separated out is filtered off and the filtrate is evaporated. The 4-n-propylphenyl 4-(4-n-propylcyclohexen-1-yl)-benzoate which remains is recrystallized from acetone; yield 9.1 g of colorless crystals, m.p. 85°, c.p. 187°.

The following are prepared analogously:
4-methylphenyl 4-(4-methylcyclohexen-1-yl)-benzoate,
4-methylphenyl 4-(4-ethylcyclohexen-1-yl)-benzoate,
4-methylphenyl 4-(4-n-propylcyclohexen-1-yl)-benzoate,
4-methylphenyl 4-(4-n-butylcyclohexen-1-yl)-benzoate,
4-methylphenyl 4-(4-n-pentylcyclohexen-1-yl)-benzoate,
4-methylphenyl 4-(4-n-hexylcyclohexen-1-yl)-benzoate,
4-methylphenyl 4-(4-n-heptylcyclohexen-1-yl)-benzoate,
4-methylphenyl 4-(4-n-octylcyclohexen-1-yl)-benzoate,
4-methylphenyl 4-[4-(1-methylhexyl)-cyclohexen-1-yl]-benzoate,
4-methylphenyl 4-[4-(2-methylbutyl)-cyclohexen-1-yl]-benzoate,
4-methylphenyl 4-[4-(3-ethylpentyl)-cyclohexen-1-yl]-benzoate, 4-ethylphenyl 4-(4-methylcyclohexen-1-yl)-benzoate,
4-ethylphenyl 4-(4-ethylcyclohexen-1-yl)-benzoate,
4-ethylphenyl 4-(4-n-propylcyclohexen-1-yl)-benzoate,
4-ethylphenyl 4-(4-n-butylcyclohexen-1-yl)-benzoate,
4-ethylphenyl 4-(4-n-pentylcyclohexen-1-yl)-benzoate,
4-ethylphenyl 4-(4-n-hexylcyclohexen-1-yl)-benzoate,
4-ethylphenyl 4-(4-n-heptylcyclohexen-1-yl)-benzoate,
4-ethylphenyl 4-(4-n-octylcyclohexen-1-yl)-benzoate,
4-ethylphenyl 4-[4-(1-methylhexyl)-cyclohexen-1-yl]-benzoate,
4-ethylphenyl 4-[4-(2-methylbutyl)-cyclohexen-1-yl]-benzoate,
4-ethylphenyl 4-[4-(3-ethylpentyl)-cyclohexen-1-yl]-benzoate, 4-n-propylphenyl 4-(4-methylcyclohexen-1-yl)-benzoate,
4-n-propylphenyl 4-(4-ethylcyclohexen-1-yl)-benzoate,
4-n-propylphenyl 4-(4-n-butylcyclohexen-1-yl)-benzoate,
4-n-propylphenyl 4-(4-n-pentylcyclohexen-1-yl)-benzoate,
4-n-propylphenyl 4-(4-n-hexylcyclohexen-1-yl)-benzoate,
4-n-propylphenyl 4-(4-n-heptylcyclohexen-1-yl)-benzoate,
4-n-propylphenyl 4-(4-n-octylcyclohexen-1-yl)-benzoate,
4-n-propylphenyl 4-[4-(1-methylhexyl)-cyclohexen-1-yl]-benzoate,
4-n-propylphenyl 4-[4-(2-methylbutyl)-cyclohexen-1-yl]-benzoate,
4-n-propylphenyl 4-[4-(3-ethylpentyl)-cyclohexen-1-yl]-benzoate, 4-n-butylphenyl 4-(4-methylcyclohexen-1-yl)-benzoate,
4-n-butylphenyl 4-(4-ethylcyclohexen-1-yl)-benzoate,
4-n-butylphenyl 4-(4-n-propylcyclohexen-1-yl)-benzoate,
4-n-butylphenyl 4-(4-n-butylcyclohexen-1-yl)-benzoate,
4-n-butylphenyl 4-(4-n-pentylcyclohexen-1-yl)-benzoate,
4-n-butylphenyl 4-(4-n-hexylcyclohexen-1-yl)-benzoate,
4-n-butylphenyl 4-(4-n-heptylcyclohexen-1-yl)-benzoate,
4-n-butylphenyl 4-(4-n-octylcyclohexen-1-yl)-benzoate,
4-n-butylphenyl 4-[4-(1-methylhexyl)-cyclohexen-1-yl]-benzoate,
4-n-butylphenyl 4-[4-(2-methylbutyl)-cyclohexen-1-yl]-benzoate,
4-n-butylphenyl 4-[4-(3-ethylpentyl)-cyclohexen-1-yl]-benzoate, 4-n-pentylphenyl 4-(4-methylcyclohexen-1-yl)-benzoate,
4-n-pentylphenyl 4-(4-ethylcyclohexen-1-yl)-benzoate,
4-n-pentylphenyl 4-(4-n-propylcyclohexen-1-yl)-benzoate,
4-n-pentylphenyl 4-(4-n-butylcyclohexen-1-yl)-benzoate,
4-n-pentylphenyl 4-(4-n-pentylcyclohexen-1-yl)-benzoate,
4-n-pentylphenyl 4-(4-n-hexylcyclohexen-1-yl)-benzoate,
4-n-pentylphenyl 4-(4-n-heptylcyclohexen-1-yl)-benzoate,
4-n-pentylphenyl 4-(4-n-octylcyclohexen-1-yl)-benzoate,
4-n-pentylphenyl 4-[4-(1-methylhexyl)-cyclohexen-1-yl]-benzoate,
4-n-pentylphenyl 4-[4-(2-methylbutyl)-cyclohexen-1-yl]-benzoate,
4-n-pentylphenyl 4-[4-(3-ethylpentyl)-cyclohexen-1-yl]-benzoate, 4-n-hexylphenyl 4-(4-methylcyclohexen-1-yl)-benzoate,
4-n-hexylphenyl 4-(4-ethylcyclohexen-1-yl)-benzoate,
4-n-hexylphenyl 4-(4-n-propylcyclohexen-1-yl)-benzoate,
4-n-hexylphenyl 4-(4-n-butylcyclohexen-1-yl)-benzoate,
4-n-hexylphenyl 4-(4-n-pentylcyclohexen-1-yl)-benzoate,
4-n-hexylphenyl 4-(4-n-hexylcyclohexen-1-yl)-benzoate,
4-n-hexylphenyl 4-(4-n-heptylcyclohexen-1-yl)-benzoate,
4-n-hexylphenyl 4-(4-n-octylcyclohexen-1-yl)-benzoate,
4-n-hexylphenyl 4-[4-(1-methylhexyl)-cyclohexen-1-yl]-benzoate,
4-n-hexylphenyl 4-[4-(2-methylbutyl)-cyclohexen-1-yl]-benzoate,
4-n-hexylphenyl 4-[4-(3-ethylpentyl)-cyclohexen-1-yl]-benzoate, 4-n-heptylphenyl 4-(4-methylcyclohexen-1-yl)-benzoate,
4-n-heptylphenyl 4-(4-ethylcyclohexen-1-yl)-benzoate,
4-n-heptylphenyl 4-(4-n-propylcyclohexen-1-yl)-benzoate,
4-n-heptylphenyl 4-(4-n-butylcyclohexen-1-yl)-benzoate,
4-n-heptylphenyl 4-(4-n-pentylcyclohexen-1-yl)-benzoate,
4-n-heptylphenyl 4-[4-(1-methylhexyl)-cyclohexen-1-yl]-benzoate,
4-n-heptylphenyl 4-[4-(2-methylbutyl)-cyclohexen-1-yl]-benzoate,
4-n-heptylphenyl 4-[4-(3-ethylpentyl)-cyclohexen-1-yl]-benzoate, 4-n-octylphenyl 4-(4-methylcyclohexen-1-yl)-benzoate,
4-n-octylphenyl 4-(4-ethylcyclohexen-1-yl)-benzoate,
4-n-octylphenyl 4-(4-n-propylcyclohexen-1-yl)-benzoate,
4-n-octylphenyl 4-(4-n-butylcyclohexen-1-yl)-benzoate,
4-n-octylphenyl 4-(4-n-pentylcyclohexen-1-yl)-benzoate,
4-n-octylphenyl 4-[4-(1-methylhexyl)-cyclohexen-1-yl]-benzoate,
4-n-octylphenyl 4-[4-(2-methylbutyl)-cyclohexen-1-yl]-benzoate,
4-n-octylphenyl 4-[4-(3-ethylpentyl)-cyclohexen-1-yl]-benzoate, 4-(2-methylbutyl)-phenyl 4-(4-methylcyclohexen-1-yl)-benzoate,
4-(2-methylbutyl)-phenyl 4-(4-ethylcyclohexen-1-yl)-benzoate,
4-(2-methylbutyl)-phenyl 4-(4-n-propylcyclohexen-1-yl)-benzoate,
4-(2-methylbutyl)-phenyl 4-(4-n-butylcyclohexen-1-yl)-benzoate,
4-(2-methylbutyl)-phenyl 4-(4-n-pentylcyclohexen-1-yl)-benzoate,
4-(2-methylbutyl)-phenyl 4-(4-n-hexylcyclohexen-1-yl)-benzoate,
4-(2-methylbutyl)-phenyl 4-(4-n-heptylcyclohexen-1-yl)-benzoate,
4-(2-methylbutyl)-phenyl 4-(4-n-octylcyclohexen-1-yl)-benzoate, 4-cyanophenyl 4-(4-methylcyclohexen-1-yl)-benzoate,
4-cyanophenyl 4-(4-ethylcyclohexen-1-yl)-benzoate,
4-cyanophenyl 4-(4-n-propylcyclohexen-1-yl)-benzoate,
4-cyanophenyl 4-(4-n-butylcyclohexen-1-yl)-benzoate,
4-cyanophenyl 4-(4-n-pentylcyclohexen-1-yl)-benzoate,
4-cyanophenyl 4-(4-n-hexylcyclohexen-1-yl)-benzoate,
4-cyanophenyl 4-(4-n-heptylcyclohexen-1-yl)-benzoate,
4-cyanophenyl 4-(4-n-octylcyclohexen-1-yl)-benzoate,
4-cyanophenyl 4-[4-(1-methylhexyl)-cyclohexen-1-yl]-benzoate,
4-cyanophenyl 4-[4-(2-methylbutyl)-cyclohexen-1-yl]-benzoate,
4-cyanophenyl 4-[4-(3-ethylpentyl)-cyclohexen-1-yl]-benzoate, trans-4-methylcyclohexyl 4-(4-methylcyclohexen-1-yl)-benzoate,
trans-4-methylcyclohexyl 4-(4-ethylcyclohexen-1-yl)-benzoate,
trans-4-methylcyclohexyl 4-(4-n-propylcyclohexen-1-yl)-benzoate,
trans-4-methylcyclohexyl 4-(4-n-butylcyclohexen-1-yl)-benzoate,
trans-4-methylcyclohexyl 4-(4-n-pentylcyclohexen-1-yl)-benzoate,
trans-4-methylcyclohexyl 4-(4-n-hexylcyclohexen-1-yl)-benzoate, trans-4-methylcyclohexyl 4-(4-n-heptylcyclohexen-1-yl)-benzoate,
trans-4-methylcyclohexyl 4-(4-n-octylcyclohexen-1-yl)-benzoate,
trans-4-methylcyclohexyl 4-[4-(1-methylhexyl)-cyclohexen-1-yl]-benzoate,
trans-4-methylcyclohexyl 4-[4-(2-methylbutyl)-cyclohexen-1-yl]-benzoate,
trans-4-methylcyclohexyl 4-[4-(3-ethylpentyl)-cyclohexen-1-yl]-benzoate, trans-4-ethylcyclohexyl 4-(4-methylcyclohexen-1-yl)-benzoate,
trans-4-ethylcyclohexyl 4-(4-ethylcyclohexen-1-yl)-benzoate,
trans-4-ethylcyclohexyl 4-(4-n-propylcyclohexen-1-yl)-benzoate,
trans-4-ethylcyclohexyl 4-(4-n-butylcyclohexen-1-yl)-benzoate,
trans-4-ethylcyclohexyl 4-(4-n-pentylcyclohexen-1-yl)-benzoate,
trans-4-ethylcyclohexyl 4-(4-n-hexylcyclohexen-1-yl)-benzoate,
trans-4-ethylcyclohexyl 4-(4-n-heptylcyclohexen-1-yl)-benzoate,
trans-4-ethylcyclohexyl 4-(4-n-octylcyclohexen-1-yl)-benzoate,
trans-4-ethylcyclohexyl 4-[4-(1-methylhexyl)-cyclohexen-1-yl]-benzoate,
trans-4-ethylcyclohexyl 4-[4-(2-methylbutyl)-cyclohexen-1-yl]-benzoate,
trans-4-ethylcyclohexyl 4-[4-(3-ethylpentyl)-cyclohexen-1-yl]-benzoate, trans-4-n-propylcyclohexyl 4-(4-methylcyclohexen-1-yl)-benzoate,
trans-4-n-propylcyclohexyl 4-(4-ethylcyclohexen-1-yl)-benzoate,
trans-4-n-propylcyclohexyl 4-(4-n-propylcyclohexen-1-yl)-benzoate,
trans-4-n-propylcyclohexyl 4-(4-n-butylcyclohexen-1-yl)-benzoate,
trans-4-n-propylcyclohexyl 4-(4-n-pentylcyclohexen-1-yl)-benzoate,
trans-4-n-propylcyclohexyl 4-(4-n-hexylcyclohexen-1-yl)-benzoate,
trans-4-n-propylcyclohexyl 4-(4-n-heptylcyclohexen-1-yl)-benzoate,
trans-4-n-propylcyclohexyl 4-(4-n-octylcyclohexen-1-yl)-benzoate,
trans-4-n-propylcyclohexyl 4-[4-(1-methylhexyl)-cyclohexene-1-yl)-benzoate,
trans-4-n-propylcyclohexyl 4-[4-(2-methylbutyl)-cyclohexen-1-yl]-benzoate,
trans-4-n-propylcyclohexyl 4-[4-(3-ethylpentyl)-cyclohexen-1-yl]-benzoate, trans-4-n-butylcyclohexyl 4-(4-methylcyclohexen-1-yl)-benzoate,
trans-4-n-butylcyclohexyl 4-(4-ethylcyclohexen-1-yl)-benzoate,
trans-4-n-butylcyclohexyl 4-(4-n-propylcyclohexen-1-yl)-benzoate,
trans-4-n-butylcyclohexyl 4-(4-n-butylcyclohexen-1-yl)-benzoate,
trans-4-n-butylcyclohexyl 4-(4-n-pentylcyclohexen-1-yl)-benzoate,
trans-4-n-butylcyclohexyl 4-(4-n-hexylcyclohexen-1-yl)-benzoate,
trans-4-n-butylcyclohexyl 4-(4-n-heptylcyclohexen-1-yl)-benzoate,
trans-4-n-butylcyclohexyl 4-(4-n-octylcyclohexen-1-yl)-benzoate,
trans-4-n-butylcyclohexyl 4-[4-(1-methylhexyl)-cyclohexen-1-yl]-benzoate,
trans-4-n-butylcyclohexyl 4-[4-(2-methylbutyl)-cyclohexen-1-yl]-benzoate,
trans-4-n-butylcyclohexyl 4-[4-(3-ethylpentyl)-cyclohexen-1-yl]-benzoate, trans-4-n-pentylcyclohexyl 4-(4-methylcyclohexen-1-yl)-benzoate,
trans-4-n-pentylcyclohexyl 4-(4-ethylcyclohexen-1-yl)-benzoate,
trans-4-n-pentylcyclohexyl 4-(4-n-propylcyclohexen-1-yl)-benzoate,
trans-4-n-pentylcyclohexyl 4-(4-n-butylcyclohexen-1-yl)-benzoate,
trans-4-n-pentylcyclohexyl 4-(4-n-pentylcyclohexen-1-yl)-benzoate,
trans-4-n-pentylcyclohexyl 4-(4-n-hexylcyclohexen-1-yl)-benzoate,
trans-4-n-pentylcyclohexyl 4-(4-n-heptylcyclohexen-1-yl)-benzoate,
trans-4-n-pentylcyclohexyl 4-(4-n-octylcyclohexen-1-yl)-benzoate,
trans-4-n-pentylcyclohexyl 4-[4-(1-methylhexyl)-cyclohexen-1-yl]-benzoate,
trans-4-n-pentylcyclohexyl 4-[4-(2-methylbutyl)-cyclohexen-1-yl]-benzoate,
trans-4-n-pentylcyclohexyl 4-[4-(3-ethylpentyl)-cyclohexen-1-yl]-benzoate, trans-4-n-hexylcyclohexyl 4-(4-methylcyclohexen-1-yl)-benzoate,
trans-4-n-hexylcyclohexyl 4-(4-ethylcyclohexen-1-yl)-benzoate,
trans-4-n-hexylcyclohexyl 4-(4-n-propylcyclohexen-1-yl)-benzoate,
trans-4-n-hexylcyclohexyl 4-(4-n-butylcyclohexen-1-yl)-benzoate,
trans-4-n-hexylcyclohexyl 4-(4-n-pentylcyclohexen-1-yl)-benzoate,
trans-4-n-hexylcyclohexyl 4-(4-n-hexylcyclohexen-1-yl)-benzoate,
trans-4-n-hexylcyclohexyl 4-(4-n-heptylcyclohexen-1-yl)-benzoate,
trans-4-n-hexylcyclohexyl 4-(4-n-octylcyclohexen-1-yl)-benzoate,
trans-4-n-hexylcyclohexyl 4-[4-(1-methylhexyl)-cyclohexen-1-yl]-benzoate,
trans-4-n-hexylcyclohexyl 4-[4-(2-methylbutyl)-cyclohexen-1-yl]-benzoate,
trans-4-n-hexylcyclohexyl 4-[4-(3-ethylpentyl)-cyclohexen-1-yl]-benzoate, trans-4-n-heptylcyclohexyl 4-(4-methylcyclohexen-1-yl)-benzoate,
trans-4-n-heptylcyclohexyl 4-(4-ethylcyclohexen-1-yl)-benzoate,
trans-4-n-heptylcyclohexyl 4-(4-n-propylcyclohexen-1-yl)-benzoate,
trans-4-n-heptylcyclohexyl 4-(4-n-butylcyclohexen-1-yl)-benzoate, trans-4-n-heptylcyclohexyl 4-(4-n-pentylcyclohexen-1-yl)-benzoate,
trans-4-n-heptylcyclohexyl 4-(4-n-hexylcyclohexen-1-yl)-benzoate,
trans-4-n-heptylcyclohexyl 4-(4-n-heptylcyclohexen-1-yl)-benzoate,
trans-4-n-heptylcyclohexyl 4-[4-(1-methylhexyl)-cyclohexen-1-yl]-benzoate,
trans-4-n-heptylcyclohexyl 4-[4-(2-methylbutyl)-cyclohexen-1-yl]-benzoate,
trans-4-n-heptylcyclohexyl 4-[4-(3-ethylpentyl)-cyclohexen-1-yl]-benzoate, trans-4-n-octylcyclohexyl 4-(4-methylcyclohexen-1-yl)-benzoate,
trans-4-n-octylcyclohexyl 4-(4-ethylcyclohexen-1-yl)-benzoate,
trans-4-n-octylcyclohexyl 4-(4-n-propylcyclohexen-1-yl)-benzoate,
trans-4-n-octylcyclohexyl 4-(4-n-butylcyclohexen-1-yl)-benzoate,
trans-4-n-octylcyclohexyl 4-(4-n-pentylcyclohexen-1-yl)-benzoate,
trans-4-n-octylcyclohexyl 4-(4-n-hexylcyclohexen-1-yl)-benzoate,
trans-4-n-octylcyclohexyl 4-[4-(1-methylhexyl)-cyclohexen-1-yl]-benzoate,
trans-4-n-octylcyclohexyl 4-[4-(2-methylbutyl)-cyclohexen-1-yl]-benzoate and
trans-4-n-octylcyclohexyl 4-[4-(3-ethylpentyl)-cyclohexen-1-yl]-benzoate.

The example which follows relates to the use, per this invention, of a phenylcyclohexene derivative of formula (I) as a component of a liquid-crystalline dielectric.

EXAMPLE 6

A liquid crystalline dielectric consisting of 19.2% of 4-(trans-4-n-propylcyclohexyl)-benzonitrile, 28.8% of 4-(trans-4-n-pentylcyclohexyl)-benzonitrile, 20.0% of 4-(trans-4-n-heptylcyclohexyl)-benzonitrile, 12.0% of 4-(trans-4-n-pentylcyclohexyl)-4'-cyanobiphenyl and 20.0% of 4-(4-n-pentylcyclohexen-1-yl)-phenetole has a melting point of $-10°$, a clear point of 68° and a viscosity of $23 \times 10^{-3}$ Pa.s. It has a positive dielectric anisotropy and is therefore suitable for use in liquid crystal display elements based on a twisted cell.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In an electrooptical display including a liquid crystalline material, the improvement wherein the liquid crystalline material comprises at least one compound of the formula

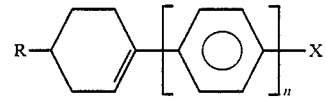

wherein n is 1 or 2, X is —H, —R, —OR, —OCOR, —OCOOR, —CF$_3$ or —F and R is alkyl of 1-8 C atoms and when two R groups are present they can be the same or different.

2. In an electrooptical display of claim 1 including a liquid crystalline material, the improvement wherein the liquid crystalline material comprises at least one compound of the formula

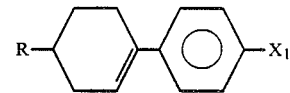

wherein $X_1$ is —R, —OR or —OCOR and R is alkyl of 1-8 C atoms.

3. In an electrooptical display of claim 1 including a liquid crystalline material, the improvement wherein the liquid crystalline material comprises at least one compound of the formula

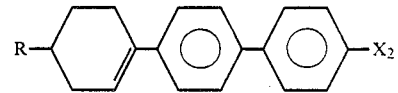

wherein $X_2$ is —H, —R, —OR, —OCOR, —F or —CF$_3$ and R is alkyl of 1-8 C atoms.

4. In an electrooptical display of claim 1 including a liquid crystalline material, the improvement wherein the liquid crystalline material comprises at least one compound of the formula

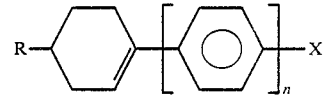

wherein n is 1 or 2, X is —H, —R, —OR, —OCOR, —OCOOR, —CF$_3$ or —F and R is alkyl of 1-8 C atoms and when two R groups are present, only one is a branched alkyl group.

5. In an electrooptical display of claim 1 including a liquid crystalline material, the improvement wherein the liquid crystalline material comprises at least one compound of the formula

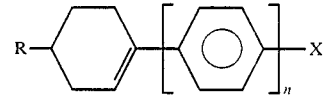

wherein n is 1 or 2, X is —H, —R, —OR, —OCOR, —OCOOR, —CF$_3$ or —F and R is alkyl of 1-8 C atoms and when two R groups are present they can be the same or different and the total number of carbon atoms in both R groups is 2-14.

6. In a liquid crystalline dielectric comprising at least two liquid crystalline components, the improvement wherein at least one component is a compound of the formula

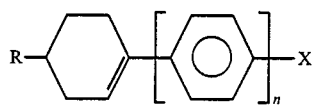

wherein n is 1 or 2, X is —H, —R, —OR, —OCOR, —OCOOR, —CF$_3$ or —F and R is alkyl of 1-8 C atoms and when two R groups are present they can be the same or different.

7. In a liquid crystalline dielectric of claim 6 the improvement wherein at least one component is a compound of the formula

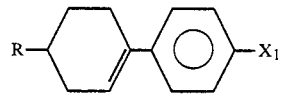

wherein X$_1$ is —R, —OR or —OCOR and R is alkyl of 1-8 C atoms.

8. In a liquid crystalline dielectric of claim 6 comprising at least two liquid crystalline components, the improvement wherein at least one component is a compound of the formula

wherein X$_2$ is —H, —R, —OR, —OCOR, —F or —CF$_3$ and R is alkyl of 1-8 C atoms.

9. In a liquid crystalline dielectric of claim 6 comprising at least two liquid crystalline components, the improvement wherein at least one component is a compound of the formula

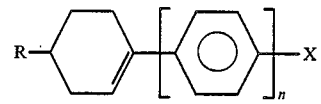

wherein n is 1 or 2, X is —H, —R, —OR, —OCOR, —OCOOR, —CF$_3$ or —F and R is alkyl of 1-8 C atoms and when two R groups are present, only one is a branched alkyl group.

10. In a liquid crystalline dielectric of claim 6 comprising at least two liquid crystalline components, the improvement wherein at least one component is a compound of the formula

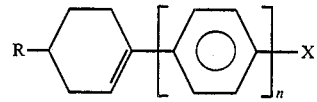

wherein n is 1 or 2, X is —H, —R, —OR, —OCOR, —OCOOR, —CF$_3$ or —F and R is alkyl of 1-8 C atoms and when two R groups are present they can be the same or different and the total number of carbon atoms in both R groups is 2-14.

11. A display of claim 3 wherein X$_2$ is R,OR or OCOR and R is alkyl of 1-8 C-atoms.

12. A display of claim 1 wherein X$_2$ is R,OR or OCOR and R is alkyl of 1-8 C-atoms.

13. A dielectric of claim 8 wherein X$_2$ is R,OR or OCOR and R is alkyl of 1-8 C-atoms.

14. A dielectric of claim 6 wherein X$_2$ is R,OR or OCOR and R is alkyl of 1-8 C-atoms.

15. A display of claim 1 wherein at least one compound is of the formula:

16. A dielectric of claim 6 wherein at least one compound is of the formula:

* * * * *